United States Patent [19]

Ashihara et al.

[11] Patent Number: 5,158,895
[45] Date of Patent: Oct. 27, 1992

[54] AUTOMATIC IMMUNOLOGICAL MEASURING SYSTEM

[75] Inventors: Yoshihiro Ashihara; Isao Nishizono, both of Tokyo; Hidetaka Minakawa, Kanagawa; Masahisa Okada, Tokyo; Yasusuke Sakurabayashi, Tokyo; Fumio Watanabe, Tokyo; Shin-ichi Wakana, Tokyo, all of Japan

[73] Assignee: Fujirebio Inc., Tokyo, Japan

[21] Appl. No.: 677,686

[22] Filed: Mar. 29, 1991

[30] Foreign Application Priority Data

Mar. 30, 1990 [JP] Japan .................................. 2-80993
May 9, 1990 [JP] Japan .................................. 2-119010
Jun. 27, 1990 [JP] Japan .................................. 2-166756
Sep. 3, 1990 [JP] Japan .................................. 2-91567

[51] Int. Cl.$^5$ .................. C12M 1/00; G01N 21/00; G01N 35/02
[52] U.S. Cl. .................................. 436/526; 436/47; 436/49; 436/807; 435/77.1; 435/287; 435/291; 435/300; 422/65; 422/67; 422/82.05
[58] Field of Search .................. 422/63, 65, 67, 82.05, 422/82.08; 435/288, 287, 291, 300, 7.1, 808; 436/47, 49, 526, 807

[56] References Cited

U.S. PATENT DOCUMENTS

| | | | |
|---|---|---|---|
| 4,383,041 | 5/1983 | Kutsusawa et al. | 435/291 |
| 4,477,578 | 10/1984 | Miles et al. | 436/47 |
| 4,731,225 | 3/1988 | Wakatake | 422/65 |
| 4,785,407 | 11/1988 | Sakagami | 364/497 |
| 4,837,159 | 6/1989 | Yamada | 436/45 |
| 4,937,048 | 6/1990 | Sakai et al. | 422/63 |
| 4,952,518 | 8/1990 | Johnson et al. | 436/518 |
| 4,988,618 | 1/1991 | Li et al. | 435/6 |

FOREIGN PATENT DOCUMENTS

| | | | |
|---|---|---|---|
| 0169434 | 1/1986 | European Pat. Off. | 436/526 |
| 0209490 | 1/1987 | European Pat. Off. | 436/526 |

*Primary Examiner*—Robert J. Warden
*Assistant Examiner*—T. A. Trembley
*Attorney, Agent, or Firm*—Sughrue, Mion, Zinn, Macpeak and Seas

[57] ABSTRACT

An automatic immunoassay apparatus utilizes cartridges each having at least two wells, a first well containing solid phase material carrying antigen or antibody, and a second well containing antibody or antigen labelled with labelling compound. The wells may be sealed with a suitable sealing film before use and the sealing film is broken when the cartridge is to be used. The cartridges are transported to a predetermined position on a steppingly movable reaction line and conveyed thereby at a predetermined interval. While the reaction line steps, a sample, labelled antigen or antibody contained in the second well and substrate, if necessary, are added to the first well and stirred at predetermined timings, and reactions between the sample and a reactive solution are measured under control of a control device having a memory storing operator selectable programs for various measuring methods.

15 Claims, 21 Drawing Sheets

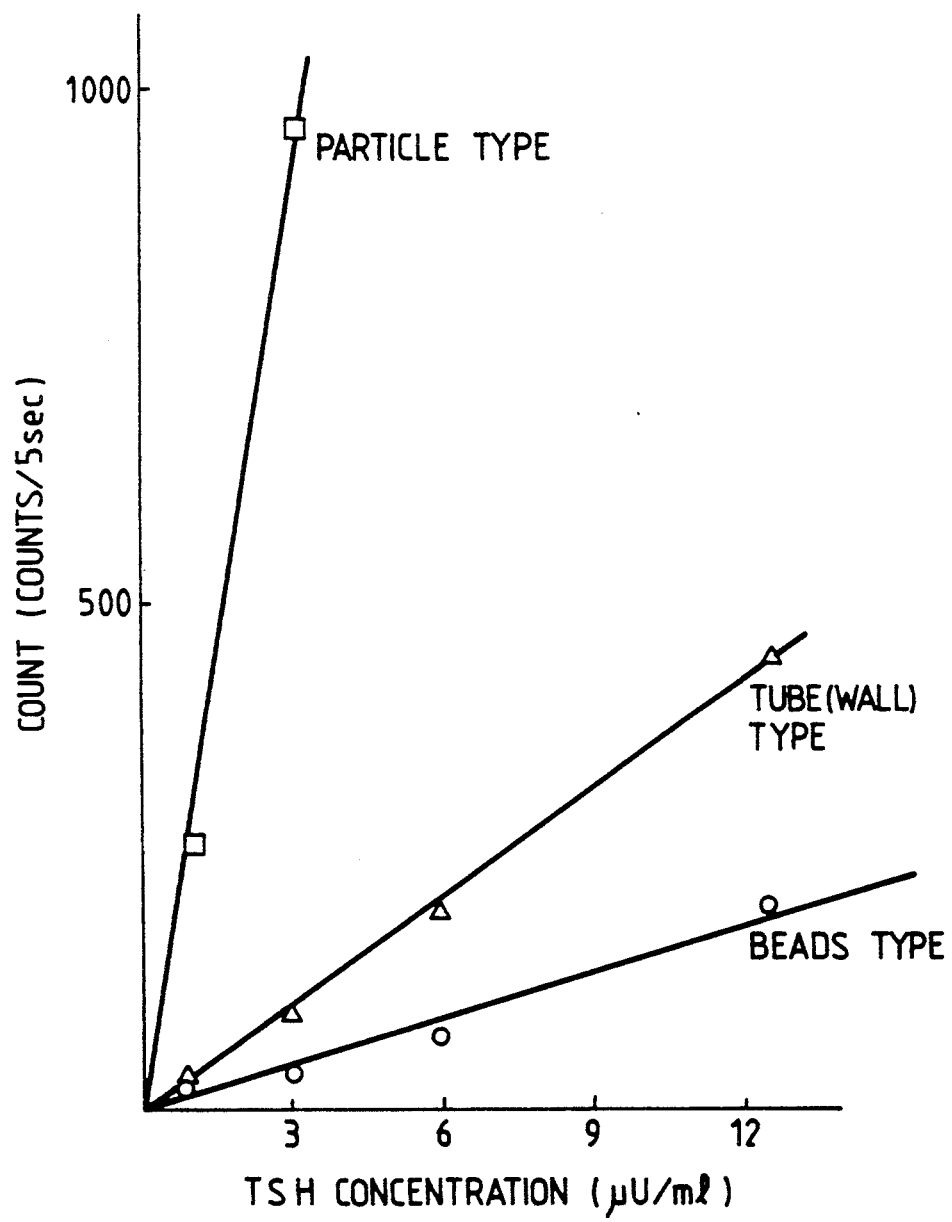

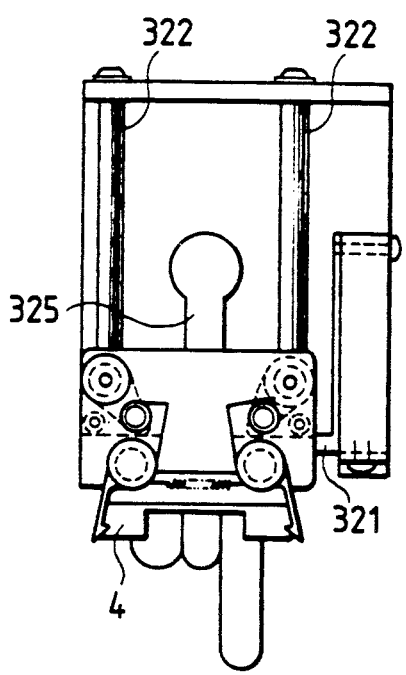
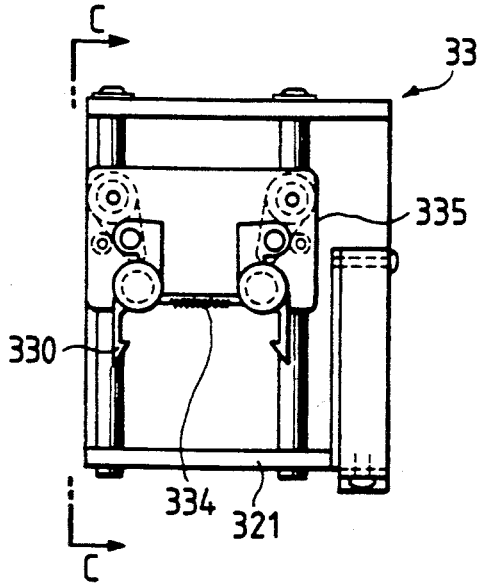
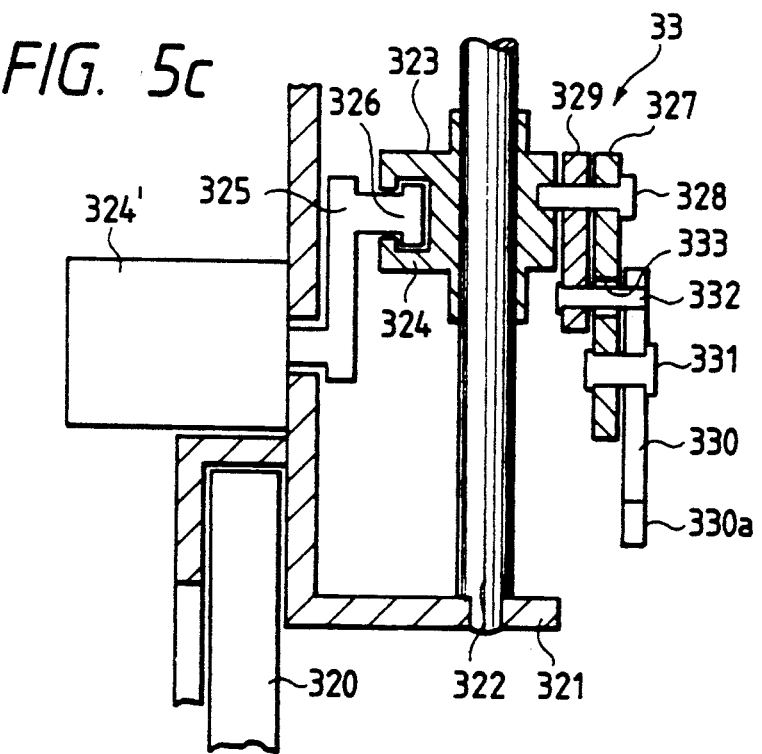

AUTOMATIC IMMUNOLOGICAL MEASURING SYSTEM

BACKGROUND OF THE INVENTION

The present invention relates to an automatic immunoassay apparatus and a method of using the same.

Immuniossay is generally performed by using various label compounds such as an enzyme a fluorescent substance such as fluorescein or rhodamine, aluminous substance such as acridinium ester, luminol or isoluminol and a radioisotope such as $^{125}I$, $^{131}I$, $^{14}C$ or $^{3}H$. Radio immunoassay using a radioactive isotope as label compound (RIA) and enzyme immunoassay using an enzyme as a label compound (EIA) are well known. Among them, EIA has been utilized widely in particular in the field of clinical test in view of its specificity and sensitivity. In EIA, it is usual to attach an antigen or antibody selected for a specific object, i.e. antibody or antigen, to be measured to solid phase material and the solid phase material carrying the selected antigen or antibody is allowed to contact with the object contained in a sample solution to thereby cause an antigen-antibody reaction to occur therebetween. Enzyme labelling reacted or bound antigen or antibody is separated from non-reacted, i.e., free enzyme labelled antigen or antibody. After the separation which is usually alled as Bind/Free (B/F) separation, the activity of enzyme labelling the reacted substance is measured, so that the measuring object in the sample is quantitatively measured.

Therefore, in order to perform EIA, a plurality of very complicated procedures, such as fractional addition of reagent, etc., dilution, agitation, B/F separation, solid phase shift, etc., are required.

As the solid phase material used in EIA, polystyrene bead, magnetic particle and inner wall surface of a reaction chamber, etc., are known.

Some improvements on EIA have been proposed. One of them is directed to an improvement of a reagent container to be used in EIA. Japanese Kokai (P) 62-273453 discloses a technique for performing EIA with high sensitivity, in which magnetic particles are used as the solid phase material and the B/F separation is performed by using a special container containing such magnetic particles and a magnetic separating device having a permanent magnet configured correspondingly to the container. Further, Japanese Kokai (P) 1-201156 discloses a technique in which a microplate for containing magnetic particles and a magnetic separator are used. Japanese Kokai (P) 63-281053 discloses a container having a plurality of wells such as reaction wells and sample wells, etc., arranged in a matrix.

On the other hand, a semi-automatic measuring device for measuring a large number of samples has been developed such as shown in E. Ishikawa, "Enzyme Immunoassay", Igaku Shoin, pages 180-207.

It has been known, however, that, in any of the known methods and apparatus, it takes 1 hour to 18 hours to perform the measurement manually even if such magnetic particle is used as the solid material. Even if the conventional semi-automatic device is used, this time can not be reduced sufficiently while some complicated procedures are still necessary as they are.

SUMMARY OF THE INVENTION

An object of the present invention is to provide an automatic apparatus for EIA or RIA, which is capable of measuring a number of identical and/or different test items which require different measuring processes, respectively, within a very short time for each item.

Another object of the present invention is to provide an immunoassay method performed by using the apparatus of the present invention.

Another object of the present invention is to provide a reaction cartridge for use in the automatic apparatus.

According to the present invention, the above objects and other objects are achieved by the provision of a full-automatic immunoassay apparatus for measuring antigen or antibody in a measuring object such as serum or tumors. The apparatus comprises a sample storing portion for storing a plurality of samples, a reagent storing portion for storing washing and/or diluent liquid, a reaction cartridge stocker portion for storing a plurality of reaction cartridges each formed preferably of plastic material such as polystyrene resin, acrylic resin, polyvinyl chloride resin or glass and integrally formed with at least two wells arranged side by side, a first of which is used to store solid phase material carrying antigen or antibody and a second of which is used to store labelling substance which is antigen or antibody labelled with label compound, a reaction line portion for moving the reaction cartridges sequentially, a reaction cartridge transporting portion for transporting the cartridges from the reaction cartridge stocker to a start location of the reaction line one by one according to a measuring item, an aspirating/fractional-pouring portion disposed at a downstream position along the reaction line for pouring each sample in the sample storing portion and the substance stored in the second well of the cartridge moved thereto to the first well of the cartridge to obtain a mixture of them, at least one stirring portion for vibrating the cartridge to stir the mixture in the first well, at least one magnetic B/F separator for magnetically separating reacted portion of the stirred mixture in the first well from non-reacted portion thereof, a washing portion for removing the non-reacted portion from the first well, a fractionally pouring/stirring portion for pouring substrate solution to the first well and stirring it, a measuring portion for optically measuring luminance information produced by a reaction between the substrate and the reacted portion in the first well, an output portion for outputting a measurement obtained in the measuring portion, a disposer portion provided around an end point of the reaction line for disposing the cartridge, the measurement for which is completed, and a control portion for controlling operations of these portions mentioned above.

Some of these consitutional components may not be used for specific measurement or the order of use of them may be changed, since immunoassay may be performed through different processes. Further, the number of wells of the cartridge as well as volumes or depths of these wells may be changed according to demand. It is well known that there are two measuring methods in general. One is the so-called "one step" method for measuring antigen or antibody and the other is the so-called "2-step" method. The one step method includes two variations each applicable to antigen or antibody measurement. In one variation, ligand and labelled antibody are added to solid phase material simultaneously and after a B/F separation is performed substrate is added thereto. In the other variation called delay method, a mixture of ligand and labelled antibody is added to solid phase material and then a B/F separation is performed followed by addition of substrate. Therefore, in the "one-step" method, the number of the wells of the cartridge may be two and a single B/F stage may be enough.

The "2-step method" is classified into antigen measuring method and antibody measuring method. In the antigen measuring method, solid phase material and ligand are mixed in a first well. After washing, enzyme labelled antibody is mixed therewith, then a B/F separation is performed and thereafter substrate is added. In the antibody measuring, antibody is diluted and then mixed with solid phase material. After washing, labelled antibody is added and, thereafter, a B/F separation is performed and then substrate is added. In the "2-step" method, a couple of the B/F devices are required and the number of the wells of each cartridge may be three.

Although the cartridge can be formed of any of the previously mentioned materials, polystyrene resin may be most preferable in view of cost and optical transparency thereof. Further, the cartridge is formed at opposite ends thereof with recesses or protrusions for stabilizing its attitude during processing and the wells should be sealed with a suitable sealing film so that reagent such as solid phase material carrying antigen or antibody can be stably stored in these wells until it is to be used. As the sealing film, aluminum foil, or various high molecular films may be used as a sole or lamination thereof. In use, the sealing film may be broken by a suitable breaker.

Further, it is possible to measure two different items of one sample simultaneously by storing solid phase material carrying different antibodies in different wells of the cartridge, repectively. Alternatively, two samples can be processed simultaneously by storing solid phase material carrying identical antibody in different wells of the cartridge. In such case, the number of wells of each cartridge should be four or more. One of these wells can be used as a diluent well in which sample is diluted.

It is preferable that the well or wells of the cartridge which receive solid phase material carrying antibody should have a larger volume and be deeper than other wells thereof to allow addition of reactive solution thereto and to facilitate an external detection of reaction.

The solid phase material usable in the present invention may be an inner wall of the well of the cartridge itself, beads or particles. Such beads may be of polystyrene. As the particles, particles of magnetic material or particles containing magnetic material are preferable. Particularly, ferrite particles may be most suitable for this purpose.

When the solid phase material is magnetic particles the B/F separation can be done in a well of the cartridge which contains such particles, by applying an external magnetic field thereto. That is, the above mentioned apparatus can be applied to any one of these methods by changing a process program stored in a memory of the control portion.

Antibody which is usable in the present invention may include medicine such as theophyline, phenytoin or valproic acid, low molecular hormone such as thyroxin, estrogen or estrdiol, cancer marker such as CEA or AFP, virus such as HIV, ATLA or HBV, high molecular hormone such as thyriod stimulating hormone (TSH) or insuline, cytocain such as IL-1, IL-2 or IL-6, growth factor such as EGF or PDGF, or antibody for DNA or RNA of the above virus. These antibodies may be monoclonal antibodies or polyclonal antibodies or may be F(ab'), Fab', Fab which are fragments of the antibody. Antigen may be virus such as HIV, ATLA, HBV, DNA of such virus, high molecular hormone such as insuline, TSH, etc.

Any of the various label compounds and radioisotopes mentioned previously may be used, although the present invention is described with using enzyme as label compound.

Such antibody or antigen can be attached to solid phase material by physical adsorption or chemical bonding. Physical adsorption is performed by reaction between the solid phase material and antigen or antibody in a suitable buffer solution. As the buffer solution, phosphate buffer solution, tris-hydrochloride buffer solution, carbonate buffer solution, etc may be used. The reaction is achieved by mixing and holding them for a certain time at 4° C. to 37° C., preferably at room temperature. The chemical attaching may be performed by using carbodiimide method among peptide attaching method. Another chemical method is a method performed in divalent cross-linking reagent such as glutaraldehyde or cyanutric chloride (cf. "Peptide Synthetic Method", Maruzen, 1975 or "Enzyme Immunoassay Method", Kyoritsu Shuppan, "Protein Nucleic acid Enzyme", special issue No. 31, 1987).

Enzyme labelled antibody to be used in EIA depends upon an object to be measured and may be an antibody recognizing epitope identical to or different from antibody attached to solid phase material. Further, for the detection of the antibody, an antibody reactive to immunoglobulin may be used. The bonding between antibody and enzyme may be obtained by known covalent bond or non-covalent bond (cf. "Protein nucleic acid enzyme", No. 31, pages 37 to 45, 1987).

Enzymes that are usable includes peroxidase, alkaliphosphatase, $\beta$- galactosidase, glucoseoxidase and substrate depends upon enzyme used and is selected from ABS, luminol-$H_2O_2$ for peroxidase, p-nitrophenylphosphate, methylunbellifenylphospate, 3-(2'-pyro-tricyclo [3.3-1.1$^{3,7}$]decan-4-methoxy-4-(3''-phosphonyloxy)phenyl-1,2-dioxetane discodium salt (AMPPD) for alkaliphosphatase, p-nitrophenyl - 0 - galactose for $\beta$- galactosidase.

Color, fluorescence or luminance is measured by a detection device from a reaction performed at 4° C. to 40° C. The enzyme immunoassay measurement can be done by using colorimetry, fluorescence or chemical luminescence. Spectrometer, photo counter, etc., or even photographic film may be used. Further, it is possible to use the so-called "Rate Method".

Although the present invention will be described in detail with reference to EIA, it should be noted that the present invention is also applicable to RIA or other methods with some modification of the measuring portion. For RIA, radioactive isotope such as $^{125}$I, $^{131}$I, $^{14}$C, $^{3}$H, etc., is used as label instead of enzyme. The same procedures as those used in EIA are used in RIA except that radioactivity is measured. In such case, radioactive labelling of antigen or antibody is easily performed by using Bolton-Hunter reagent. For example, it can be prepared by adding the Bolton-Hunter reagent to antigen or antibody solution dissolved in a 0.1 M sodium hydrogen carbonate aqueous solution, and after 1 to 2 hours, removing unreacted Bolton-Hunter reagent by using a desalting column of G-25, etc. Further, radioactive labeling of $^{125}I$ can be easily carried out by employing the chloramine T method or the iododine method. For effecting the immuno reaction, a sample is added to the solid phase material and reacted at 4° C. to 40° C., preferably at 20° C. to 38° C., for 1 to 18 hours, washed with a physiological salt solution or distilled water and then counting its radioactivity. A scintillation counter can be used for the measurement.

It should be noted that the above procedures can be manually performed with respect to each of the cartridges according to the presnt invention. That is, the structure of the cartridge itself should fall in the scope of the present invention.

BRIEF DESCRIPTION OF THE DRAWINGS

FIG. 1b is a cross section of the cartridge shown in FIG. 1a;

FIG. 1f shows results of measurement using the cartridges according to the present invention;

FIGS. 5A to 5C show a pick-up device used in the apparatus;

DETAILED DESCRIPTION OF THE PREFERRED EMBODIMENTS

Figure 1:
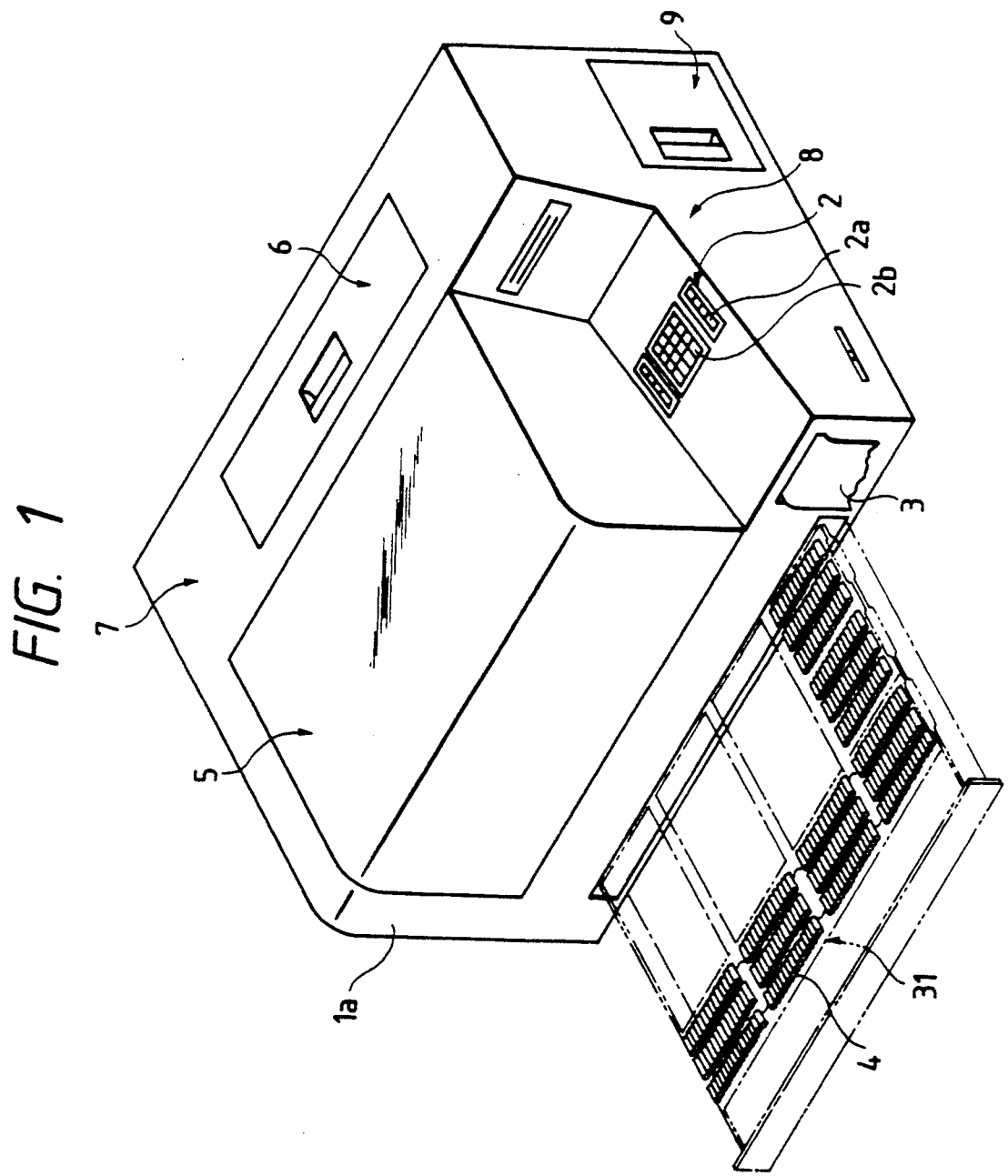
FIG. 1. is a perspective view of an outer configuration of an automatic EIA apparatus according to the present invention.

FIG. 1 is a perspective view of an automatic enzyme immunological measuring apparatus according to the present invention.

In FIG. 1, the automatic enzyme immunological measuring apparatus 1 includes a housing 1a in a lower portion of which a cartridge stocker 30 is disposed removably. The cartridge stocker 30 stocks a plurality of cartridges 4 in row and column matrix. An input portion 2 including a start button 2a and measuring selection buttons 2b, etc., is arranged in one side of the housing 1a and an output portion 3 is arranged in a front panel of the housing 1a. A processing portion 10 (FIG. 2) for performing a series of operations of mixing sample with enzyme-labelled substance and substrate, stirring them, causing reaction between them and measuring the reaction is arranged in an upper portion of the housing 1a. A transporting portion for transporting the cartridges and a control portion for controlling the series operations, etc., which are not shown, are housed in the housing 1a.

Figure 2:
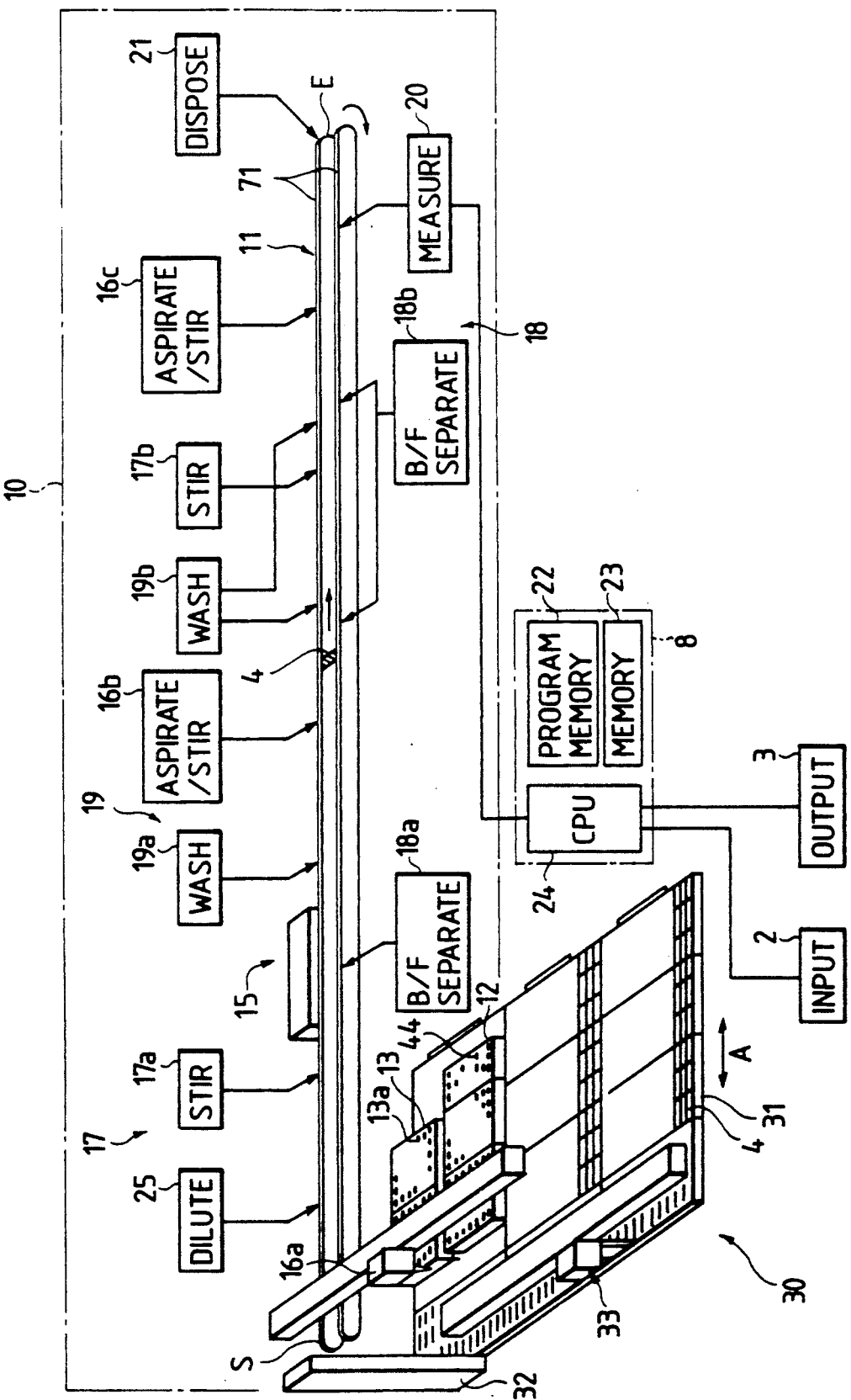
FIG. 2 is a perspective view showing an inside construction of the apparatus schematically.

FIG. 2 shows an inside construction of the housing 1a schematically. In FIG. 2, the housing includes a lower level and an upper level. The processing portion 10 includes, in the upper level, a reaction line 11 composed of a pair of parallel endless conveyer belts 71 driven by a stepping motor along which the cartridges 4 are moved sequentially. A diluting portion 25, a stirring portion 17, a magnetic separator portion 18, a washing portion 19, aspirating/pouring/stirring portion 15, a measuring portion 20 and a discharging portion 21 are arranged in substantially this order along the reaction line 11.

A sample stocker 12 is provided in the upper level which stores a plurality of samples 44 and a chip stocker 13 for storing a plurality of chips 13a is also provided in the upper level adjacent to the sample stocker 12.

The aspirating/fractionaly pouring portion 16 includes a plurality of aspirator/pouring devices 16a, 16b and 16c arranged suitably along the reaction line 11 for aspirating a predetermined amount of sample to a chip 13a by means of a suitable pump means, pouring it to a reaction well of a cartridge 4 transferred onto the reaction line 11, aspirating enzyme-labelled substance from an enzyme-labelled substance well 4b or 4c of the cartridge 4 and pouring it to the reaction well thereof to thereby obtain a mixture liquid of them.

The stirring portion 17 stirs the mixture in the reaction well of the cartridge so that enzyme immunological reaction occurs. The stirring portion 17 includes a plurality of stirrers 17a and 17b arranged suitably along the reaction line 11.

The magnetic separator 18 comprises a plurality of separators 18a and 18b arranged in suitable positions along the reaction line.

The washing portion 19 includes a plurality of washing devices 19a and 19b arranged in suitable positions along the reaction line.

The components mentioned above operate under control of a control portion 8 (FIG 2) having a program memory 22 containing programs for different enzyme immunological measurements, such as one-step measurement, two-step measurement, delayed reaction measurement and two-step measurement with diluent, etc. The control portion 8 further includes a memory 23 for storing informations necessary to obtain immunological information from an output data of the measuring portion 20 and a CPU 24 connected in one side to the output of the measuring portion 20 and in the other side to an input portion 2 and an output portion 3. The CPU 24 controls an operation of the control portion 22 itself. The output portion 3 may comprise a plotter and a display.

These components mentioned above will be described in detail later, individually, with reference to FIG. 2, FIG. 3 which is a detailed plan view of the apparatus shown in FIG. 2 and FIG. 4 which is a partial cross sectional view along a line IV—IV in FIG. 3.

As mentioned previously, the role of the cartridge itself is very important in this invention. Therefore, the cartridge will be described first in detail with reference to FIGS. 1a to 1e and then the preparation thereof and its effect will be described.

Figure 1A:
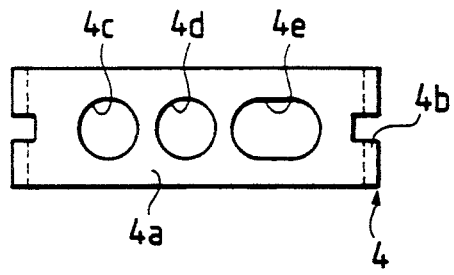
FIG. 1a is a plan view of a cartridge according to the present invention.
Figure 1D:
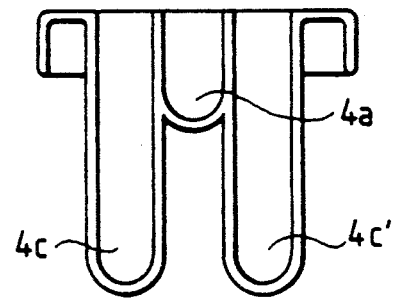
FIGS. 1c to 1e are cross sections of other embodiments of the cartridge according to the present invention, respectively.
Figure 1B:
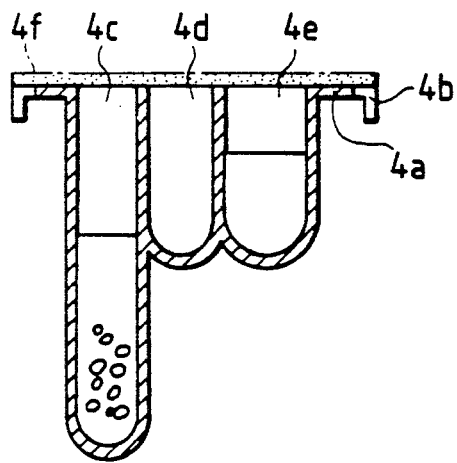

As shown in FIGS. 1a and 1b, the cartridge 4 includes a substantially rectangular plate portion 4a having its longitudinal ends 4b notched. These notched ends are to make the cartridge to be transported stably. Therefore, any protrusions may be formed on the plate portion 4a instead of the notches.

Figure 1E:
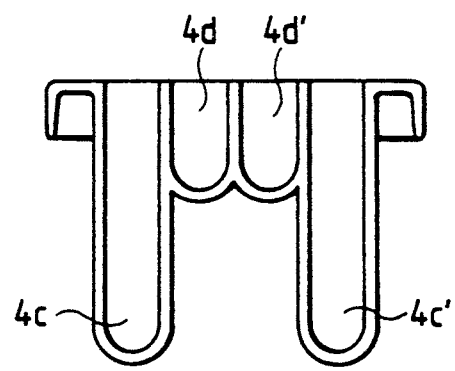
Figure 1C:
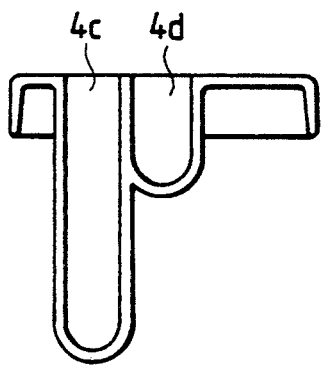

At least two wells are formed in the rectangular plate portion 4a side by side lengthwise direction as shown in FIG. 1c, although the cartridge 4 shown in FIG. 1a includes three wells 4c, 4d and 4e. A configuration and depth of each well may be arbitrarily selected depending upon specific application intended. However, at least one (4c) of these wells is made deeper than others for the purpose to be described later. The well 4c is preliminarily filled with solution containing solid phase material to which antigen or antibody is attached. The solid phase is particles or an inner wall thereof may be used as solid phase as mentioned previously. In order to reserve such solution stably, at least the well 4c is sealed by a sealing material 4f which may be aluminum foil, high molecular film, individually or in laminated form. The seal 4f is broken by a suitable breaker when it is to be used.

The cartridge 4 is formed from resin such as polystyrene resin, as mentioned previously. Instead of the notched ends 4b, protrusions may be provided. Variations of the cartridge 4 are shown in FIGS. 1c, 1d and 1e, respectively. In FIG. 1c, the cartridge 4 has two wells corresponding to the wells 4c and 4d in FIG. 1a, which can be used when any diluting operation is not required. In FIG. 1d, the cartridge 4 has three wells with the center well having the smallest depth and the other wells each corresponding to the well 4c in FIG. 1a being filled with identical antigen or antibody attached solid phase material. This cartridge is suitable to measure two kinds of serum simultaneously. When these deeper wells are filled with different antigen attached solid phase materials, it can be used to measure two kinds of objects simultaneously. FIG. 1e shows the cartridge having 4 wells. This is usable to measure two kinds of object simultaneously with diluting operation.

Returning to FIGS. 1a and 1b, the well 4e is filled with serum or diluting liquid and available for reaction or diluting operation and the well 4c is used for reaction in detection of antigen or for diluting operation for antibody detection.

Now, a preparation of such cartridge will be described starting from a preparation of solid phase.

I—Preparation of Cartridge

1—carboxylated-ferrite particles

Carboxylated ferrite particles can be obtained by adding 50 ml of 3-aminopropyltriethoxysilane to 5 g of ferrite particles (polystyrene having an average particle size of the core of 0.3 μm) which had been previously washed 5 times for each 60 seconds with distilled water by using an ultrasonic washing machine (Batt type, manufactured by Nippon Seiki Seisakusho K.K.), further adding 30 ml of glacial acetic acid to react at room temperature for 3 hours, followed by washing and reacting with glutaric acid anhydride. Glacial acetic acid was added dropwise under ice-cooling and stirring, and washing was carried out each three times with distilled water, methanol and distilled water, and further five times with each 300 ml of 0.1 M sodium hydrogen carbonate solution. The reaction with glutaric acid was carried out by adding 2.85 g of glutaric acid anhydride to 100 ml of 5% by weight (0.1 M sodium hydrogen carbonate solution) particles and reacting for 10 minutes. After completion of the reaction, the mixture was washed three times with each 300 ml of 0.1 M sodium hydrogen carbonate solution, and further five times with distilled water. This was used as carboxylated ferrite particles.

2—Solid Phase: anti-TSH attached carboxylated-ferrite particles

In 5 ml of 20 mM phosphate buffer (pH 4.5) was dispersed 50 mg of carboxylated ferrite particles prepared in I-1, followed by adding 50 mg of water-soluble carbodiimide. After reacting at room temperature for 20 minutes, the supernatant was removed, and 5 ml of anti-TSH mouse IgG solution (1 mg/ml, 0.002 M phosphate buffer solution, pH:4.5), and the mixture was stirred by an end-over-end mixer. After 2 hours, these particles were washed five times with 2% BSA solution (0.1 M Tris-HCl, 1 mM $MgCl_2$, pH: 7.5) and dispersed in the similar BSA solution to obtain anti-TSH-mouse IgG sensitized carboxylated-ferrite particles.

3—Solid phase: Anti-TSH-Mouse-IgG bound wall surface of well

In the first well 10b of the cartridge 10 in FIG. 1b, 200 μl of anti-TSH-mouse IgG solution (4 μg/ml, 10 mM phosphate buffer, pH 7.0) was poured and maintained it for 18 hours at room temperature. The well was washed three times with physiological salt solution and then 300 μl of 2% BSA solution (0.1 M Tris-HCl, 1 mM $MgCl_2$, pH 7.6) was added thereto, resulting in a cartridge having a well bound with anti-TSH-mouse-IgG bound well.

4—Solid Phase anti-TSH-mouse-IgG bound polystyrene beads 100 polystyrene beads of ⅛ inch were immersed in 25 ml of anti-TSH-mouse-IgG solution (4 μg/ml, 10 mM phospate buffer) and maintained at room temperature for one night. These beads were washed three times with physiological salt solution and then 25 ml of 2% BSA solution (the same as that mentioned above) was added thereto, resulting in anti-TSH-mouse-IgG bound polystyrene beads.

II—Preparation of Cartridge for TSH Measurement

1—Particle type cartridge

250 μl of anti-TSH-mouse-IgG bound ferrite particle (0.04% particle) prepared in I-2 was poured to the well 4c of the cartridge 4 in FIG. 1b and 100 μl of alkaliphosphatase attached anti-TSH-mouse-IgG-Fab solution (containing 0.1 M Tris-HCl, 0.1 mM ZnC$_2$, 1 mM MgCl$_2$, pH 7.5, 2% BSA, 500 ng/ml alkaliphosphatase attached anti TSH mouse IgG-Fab) was poured to the second well 4d. These wells of the cartridge were covered by an aluminum foil having a polyvinyl chloride coated adhesion surface and heat sealed. The resultant cartridge was used as particle type TSH measuring cartridge.

2—Wall type Cartridge

100 μl of alkaliphosphatase attached anti TSH mouse IgG-Fab solution (containing 0.1 M Tris-HCl, 0.1 mM ZnCl$_2$, 1 mM MgCl$_2$, pH 7.5, 2% BSA, 500 ng/ml alkaliphosphatase attached anti TSH mouse IgG-Fab) was added to the well 4d containing anti TSH mouse IgG prepared in II-1. The cartridge was heat sealed by an aluminum foil having an adhesion surface coated with polyvinyl chloride.

3-Beads type Cartridge

One of anti TSH mouse IgG attached polystyrene beads prepared in II-1 was put in the well 4c and 250 μl of 2% BSA solution was added thereto. Then, 100 μl of alkaliphosphatase phosphatase bound anti TSH mouse IgG-Fab solution (containing 0.1 M Tris-HCL, 0.1 mM ZnCl$_2$, 1 mM MgCl$_2$, pH 7.5, 2% BSA, 500 ng/ml alkaliphosphatase bound anti TSH mouse IgG Fab) was poured to the well 4e. The cartridge was heat-sealed by an aluminum foil having polyvinyl chloride coated adhesive surface.

III—Preparation of Cartridge

1—HTLV-I antigen attached ferrite particles

Ferrite particles available from Nippon Paint K.K. was dispersed in 800 μl at 10% concentration to which 2 ml of HTLV-I antigen (400 μg/ml) was added, followed by stirring in an end-over-end mixer at room temperature for one night. The particles were washed 5 times with 2% BSA solution (0.1 M Tris-HCl, 1 mM MgCl$_2$, pH 7.5) and dispersed in same BSA solution, resulting in HTLV-I antigen bound ferrite particles.

IV—Preparation of Cartridge for HTLV-I Antibody Detection

350 μl of HTLV-I antigen bound ferrite solution (0.008%/particle/BSA solution) prepared in III-1 was poured to the well 4c and then 300 μl of anti human IgG mouse IgG bound alkaliphosphatase was poured to the well 4. The cartridge was heat-sealed by an aluminum foil having polyvinyl chloride coated adhesive surface.

V—Measurement of TSH

The seals on the wells 4c, 4d and 4e were broken by the seal breaker and then a sample containing 50 μl of TSH (0, 10 μU/ml) and 50 μl of anti TSH Fab' attached alkaliphosphatase phosphatase conjugate (conjugate concentration 0.5 μg/ml, 0.1 M Tris-HCl, 2%BSA, 1 mM MgCl$_2$, 0.1 mM ZnCl$_2$, pH 7.5) contained in the well 4c were added to the well 4d and mixed.

1—Measurement of bead type TSH mesasuring well

After ten minutes, 30 μl of the mixture contained in the well 4c was added to the well 4d containing beads and stirred. After 10 minutes, supernatant was removed by aspiration and washed 4 times with physiologica salt solution. 300 μl of substrate solution containing 100 μg/ml of AMPPD (0.1 M Tris-HCl, 1 uM MgCl$_2$, 0.1 mM ZnCl$_2$, pH 9.8) was added and allowed to react at room temperature. After reaction for 10 minutes, the reaction was measured by a luminometer (Aroka K.K.). The result is shown in FIG. 1f.

2—Measurement of wall type TSH measuring well

After 10 minutes, 30 μl of the mixture contained in the well 4c was added to the well 4d attached with antibody and stirred. After 10 minutes, supernatant was removed by aspiration and washed 4 times with physiological salt solution. 300 μl of AMPPD solution used in V-1 was added to the well 4c and allowed to react at room temperature. Then, after 5 minutes, the reaction was measured by the luminometer. The result is shown in FIG. 1f.

3—Measurement of the particle type TSH measuring well

After 10 minutes, 30 μl of the mixture contained in the well 10c was added to the well 4c containing antibody bound particles, stirred and put as it is for 10 minutes. The well 4c was faced to a permanent magnet whose surface magnetic field is 3000 Gauss to attract the particles. Supernatant was removed by aspiration and, after pouring physiological salt solution to the well 4c, ferrite particles were attracted by the same magnet and supernatant was removed by decantation. This processing was repeated by 4 times. 300 μl of AMPPD used in V-1 was added to the well 4c and allowed to react for 5 minutes at room temperature and then luminance was measured by the luminometer. The result is shown in FIG. 1f.

VI—Measurment of HTLV-I Antibody with Using the HTLV-I

Well

The seal on the well 4c was broken by the seal breaker to which 20 μl of serum was added. Further, 180 μl of diluent solution (0.1 M Tris-HCl, 1 mM MgCl$_2$, 0.1 mM ZnCl$_2$ pH 7.0 containing 10% NRS, 2% BSA) was added thereto. 20 μl of diluted serum was mixed with HTLV-I antigen attached particles in the well and after being stirred put as it is at 37° C. for 10 minutes. The well 4d was faced to a permanent magnet whose surface magnetic field is 3000 Gauss to attract the particles. Supernatant was removed by aspiration and 400 μl of 4% physiological salt solution was added to the well 4c and stirred. Ferrite particles was attracted by the same magnet and supernatant was removed by aspiration. This processing was repeated by 2 times.

250 μl of anti human IgG mouse IgG bound alkali phosphatase solution (300 ng/ml protein solution) was added to the well 4c and put as it is for 10 minutes. The well 4c was faced to a permanent magnet whose surface magnetic field is 3000 Gauss to attract the particles. Supernatant was removed by aspiration and,then, 400 μl of 0.4% physiological salt solution was added and stirred. Ferrite particles was attracted by the same magnet and supernatant was removed by aspiration. This processing was repeated by 4 times. 300 μl of AMPPD used in V-1 was added to the well 4c and allowed to react for 5 minutes at room temperature and then luminance for 5 seconds was measured by the luminometer. The result is shown in Table 1.

TABLE 1

| Sample | Measurement of HTLV-I antibody | |
|---|---|---|
| | | Count Number ($\times 10^3$)(counts/5 sec) |
| only buffer | 1 | 0.005 |
| | 2 | 0.011 |
| | 3 | 0.009hz.1/32 |

| | CA19-9 Measurement | |
|---|---|---|
| Serum Sample | Count Number ($\times 10^3$) (counts/5 ml) | Amount of CA19-9 ($\mu$U/ml) |
| 1 | 0.208 | 1.9 |
| 2 | 1.408 | 19.3 |
| 3 | 4.560 | 59.5 |
| 4 | 2.144 | 31.6 |
| 5 | 8.575 | 108.9 |

VII—Measurement of CA19-9

1—Preparation of CA19-9 antibody bound particles

In a similar manner to II, anti CA 19-9 MCA sensitized ferrite particles were prepared by reacting 2 mg of anti CA19-9 monoclonal antibody (MCA) and washing it sufficiently (0.004% particle/2%BSA, 0.1 M Tris-HCl, 1 mM $MgCl_2$, 0.1 mM $ZnCl_2$, pH 7.5).

2—Preparation of cartridge for particle type CA19-9 measurement

250 μl of anti CA19-9 mouse IgG sensitized ferrite particles were added to the well 4c of the cartridge 4 in FIG. 1c and 350 μl of alkali phosphatase sensitized anti CA19-9 mouse IgG-Fab solution (0.5 μg/ml) was added to the well 4d. The cartridge was heat sealed by a PET laminated aluminum foil.

3—Measurement of CA19-9

The aluminum seal used in VII-2 was preliminarily broken by the seal breaker and 20 μl of serum was added to the well 4c and after being stirred put as it is for 10 minutes. Then, The well 4c was faced to a permanent magnet whose surface magnetic field is 3000 Gauss to attract the particles. Supernatant was removed by decantation and, then, 0.2% physiological salt solution was added and stirred. Ferrite particles were attracted by the same magnet and supernatant was removed in a similar manner. This processing was repeated by 2 times. Then, 250 μl of the labelled antibody solution in the well 4d was added to the well 4c and stirred. After 10 minutes at room temperature, the ferrite particles were attracted and supernatant was removed. The processing was repeated 4 times. Then, 300 μl of same substrate solution used in IV was added and stirred. After 5 minutes at room temperature, luminance for 5 seconds was measured by the luminometer. The result is shown in Table 2.

TABLE 2

| | CA19-9 Measurement | |
|---|---|---|
| Serum Sample | Count Number ($\times 10^3$) (counts/5 sec) | Amount of CA19-9 ($\mu$U/ml) |
| 1 | 0.208 | 1.9 |
| 2 | 1.408 | 19.3 |
| 3 | 4.560 | 59.5 |
| 4 | 2.144 | 31.6 |
| 5 | 8.575 | 108.9 |

VIII—Preparation of Cartridge for Particle Type CA19-9 Measurement

250 μl of anti CA19-9 mouse IgG sensitized ferrite particles prepared in VII-1 were added to the wells 4c and 4c' of the cartridge 4 in FIG. 1d and 350 μl of alkaliphosphatase sensitized anti CA19-9 mouse IgG-Fab solution (0.5 μg.ml) were added to the well 4e. These wells were heat sealed by a PET laminated aluminum foil.

1—Measurement of CA19-9

The aluminum seal used in VIII was preliminarily broken by the seal breaker and each 20 μl of different serums were added to the wells 4c and 4c', respectively, and after being stirred put as they are for 10 minutes. Then, The wells were faced to a permanent magnet whose surface magnetic field is 3000 Gauss to attract the particles. Supernatant was removed by decantation and,then, 0.2% physiological salt solution was added and stirred. Ferrite particles were attracted by the same magnet and supernatant was removed in a similar manner. This processing was repeated 2 times. Then, 250 μl of the labelled antibody solution in the well 4d was added to the wells 4c and 4c' and stirred. After 10 minutes at room temperature, the ferrite particles were attracted and supernatant was removed. 400 μl of washing liquid was added and stirred and the ferrite particles were attracted again by the same magnet and supernatant was removed. The processing was repeated 4 times. Then, 300 μl of same substrate solution used in IV was added and stirred. After 5 minutes at room temperature, luminance for 5 seconds was measured by the luminometer. The result is shown in Table 3.

TABLE 3

| | | Assay of Ca19-9 | |
|---|---|---|---|
| Sample | Cartridge Well | Sample No. | Count Number ($\times 10^3$) (counts/5 sec) |
| serum | 13 | 1 | 1.628 |
| | | 2 | 0.826 |
| | | 3 | 0.421 |
| | 15 | 4 | 0.126 |
| | | 5 | 0.543 |
| | | 6 | 0.968 |

IX—Preparation of HBs Antigen Sensitized Ferrite Particles

Ferrite particles available from Nippon Paint K.K. were dispersed in 800 μl at 5% concentration to which 2 ml of HBs antigen (400 μg/ml) was added, followed by stirring in an end-over-end mixer at room temperature for one night. The particles were washed 5 times with 2% BSA solution (0.1 M Tris-HCl, 1 mM $MgCl_2$, pH 7.5) and dispersed in same BSA solution, resulting in HBs antigen sensitized ferrite particles.

X—Preparation of Cartridge for Particle Type HTLV-I and HBs Antibody Detection 350 μl of HTLV-I antigen sensitized ferrite solution (0.008%/particle/BSA solution) prepared in III was poured to the well 4c of the cartridge 4 in FIG. 1e and 350 μl of HBs antigen sensitized ferrite solution (0.008%/particle/BSA solution) prepared in IX was added to the well 4d. Then 300 μl of anti human IgG mouse IgG sensitized alkaliphosphatase was poured to the well 4d. The cartridge was heat-sealed by an aluminum foil.

XI—Measurement of HTLV-I and HBs

The seal on the wells 4c, 4c', 4d and 4d' of the cartridge prepared in V were broken by the seal breaker and 20 μl of serum was added to the well 4d'. Further, 180 μl of diluent solution (0.1 M Tris-Hcl, 1 mM $MgCl_2$, 0.1 mM $ZnCl_2$, pH 7.0 containing 10% NRS, 2% BSA) was added thereto. Each 20 μl of this diluted serum was mixed with HTLV-I antigen sensitized particles in the well 4c and the HBs antigen sensitized particles in the well 4c'. After being stirred, these wells were put as they are at 37° C. for 10 minutes. Then, these wells were faced to a permanent magnet whose surface magnetic field is 3000 Gauss to attract the particles. Supernatant was removed by decantation and,then, 0.4% physiological salt solution was added and stirred. Ferrite particles were attracted by the same magnet and supernatant was removed in a similar manner. This processing was repeated by 2 times.

Each 250 μl of anti human IgG mouse IgG sensitized alkaliphosphatase solution (300 ng/ml protein solution) was added to the wells 4c and 4c' and put as they are for 10 minutes. The ferrite particles were attracted by the same magnet again and supernatant was removed by aspiration. 400 μl of 0.4% physiological salt solution was added and stirred and the ferrite particles were attracted again by the same magnet and supernatant was removed. The processing was repeated 4 times. Then 300 μl of same AMPPD solution used in V-1 was added and stirred. After 5 minutes at room temperature, luminance for 5 seconds was measured by the luminometer. The result is shown in Table 4.

TABLE 4

| | | Measurement of HTLV-I and HBs antibody | |
|---|---|---|---|
| | | Count Number ($\times 10^3$)(counts/5 sec) | |
| Sample | | Well 15 (HTLV-I) | Well 16 (HBs) |
| only buffer | 1 | 0.006 | 0.002 |
| | 2 | 0.017 | 0.009 |
| | 3 | 0.006 | 0.012 |
| | 4 | 0.009 | 0.006 |
| | 5 | 0.015 | 0.007 |
| negative serum | 1 | 0.052 | 0.125 |
| | 2 | 0.072 | 0.132 |
| | 3 | 0.059 | 0.115 |
| | 4 | 0.078 | 0.131 |
| positive serum | 1 | 0.726 | 0.926 |
| | 2 | 0.718 | 12.821 |
| | 3 | 1.526 | 8.643 |

The cartridges prepared suitably as described are used in the apparatus. Now, the apparatus will be described in detail with reference to FIGS. 3 to 17.

Cartridge Stocker

Figure 3:
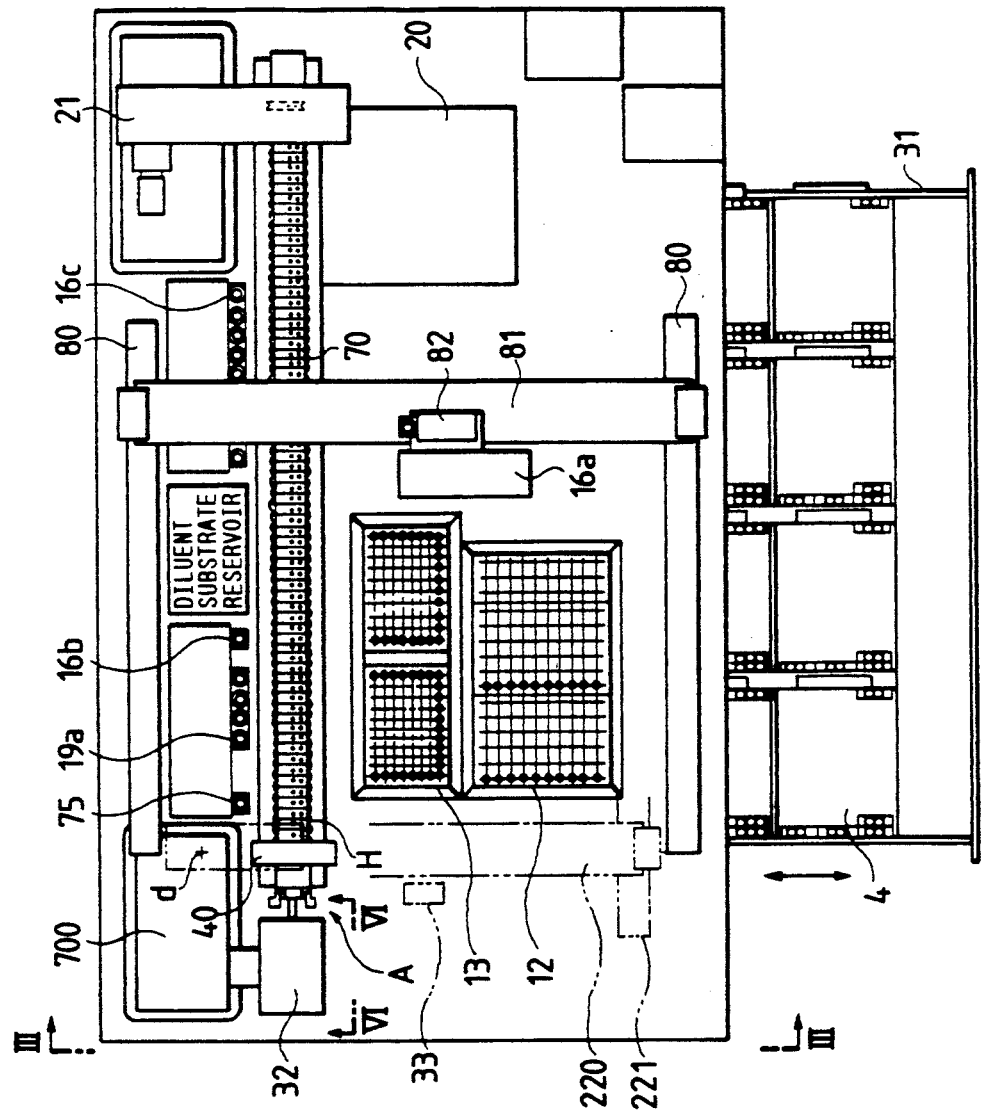
FIG. 3 is a plan view of the inside construction of the apparatus shown in FIG. 2.

The cartridge stocker 31 stocking a plurality of the cartridges 4 in row and column matrix is removably inserted horizontally into the lower level portion of the apparatus shown in FIG. 3.

Cartridge Transportation Mechanism

Figure 4:
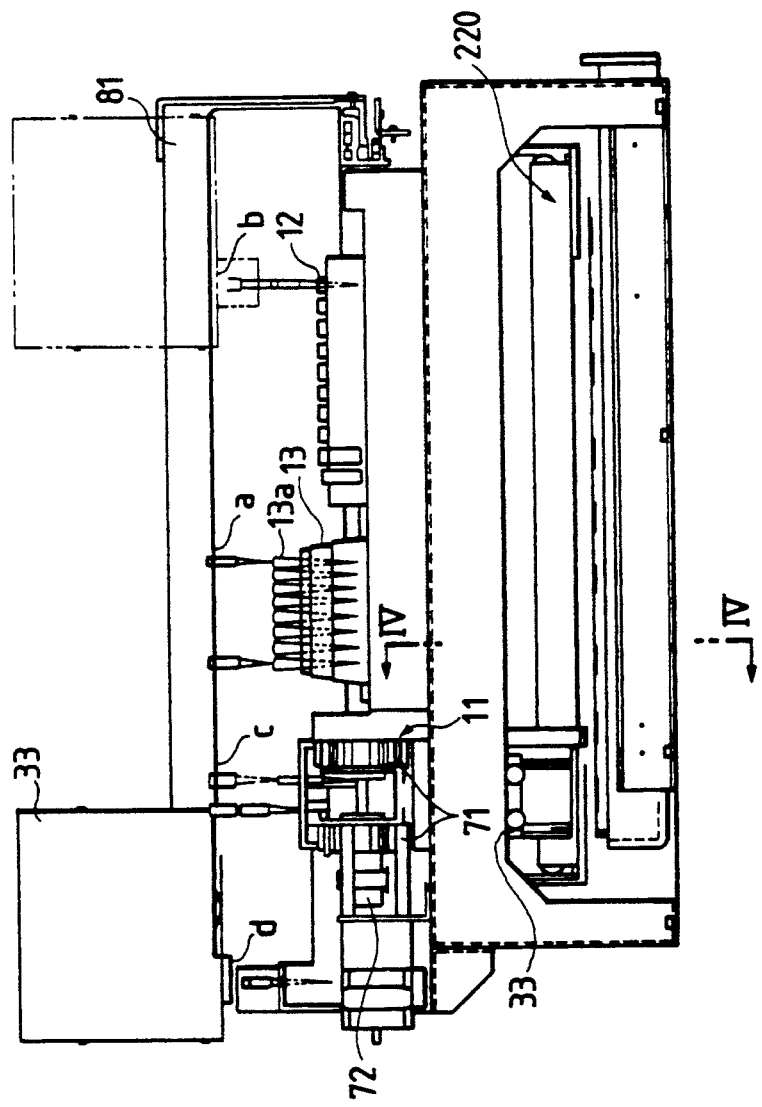
FIG. 4 is a partial cross section taken along a line IV—IV in FIG. 3.

As shown in FIGS. 3 and 4, a cartridge transportation mechanism is arranged over the cartridge stocker 31. The mechanism extends along an insertion direction of the cartridge stocker 31 and is composed of a pair of rails 221 arranged perpendicularly to the extending direction and a crane arm 220 movable along the rails 221. A cartridge pick-up device 33 is mounted on the arm 220 movably therealong.

A mechanism for moving the arm 220 along the rails 221 and moving the pick-up device 33 along the arm 220 can be realized in any known mechanism such as used in a X-Y plotter. In this embodiment, the mechanism is realized by using reversible motors (not shown), pulleys (not shown) and wires arranged in a known manner.

These reversible motors are controlled by a suitable control mechanism such that the pick-up device 33 is moved to a predetermined position (shown by A in FIG. 3) so that the cartridges 4 arranged in X-Y matrix on the cartridge stocker 31 can be shifted one by one to that position

Pick-Up Device

The pick-up device 33 is shown in FIGS. 5A to 5C in detail. The pick-up device 33 includes a vertically movable hook device. FIG. 5A is a front view of the hook device shown at an upper position. It is moved down to catch opposite ends of a cartridge 4 as shown in FIG. 5B. FIG. 5C is a side view of the pick-up device 33. In FIGS. 5A to 5C, the pick-up device 33 is moved to a position in which a selected cartridge 4 is disposed while holding the hook device in the state shown in FIG. 5B and when the pick-up device 33 reaches the certain cartridge 4 on the cartridge stocker 31, the hook device thereof is further lowered to catch the cartridge and then moved to the predetermined position A. At the position A, the pick-up device 33 is further lowered to put the cartridge 4 in the predetermined position A.

The pick-up device 33 includes a generally C shaped frame 321 slidably engaged with the arm 320 and a pair of vertical rods 322 provided in parallel between opposite end portions of the C shaped frame 321. A slider member 323 is slidably mounted on the rods 322. As shown in FIG. 5C, a lateral groove 324 is formed in a rear side surface of the slider member 323 and a motor 324' is fixedly mounted on the frame 321. An end of an arm 325 is fixedly connected to a shaft of the motor 324' and the other end of the arm 325 is formed with a protrusion 326 which is slidably fitted in the lateral groove. Thus, with rotation of the motor 324, the protrusion 326 of the arm 325 slides along the lateral groove 324, so that the slider member 323 is vertically driven.

A plate member 327 is fixedly secured to a front portion of the slider member 323 with a suitable gap therebetween. The gap is given by pins 328. A pair of cam levers 329 are arranged between the slider member 323 and the plate member 327 such that the levers 329 can be swung about the pins 328.

A pair of hook members 330 are mounted on the front surface of the plate member 327 rotatably about pins 331, respectively. Hooks 330a are formed in lower end portions of the hook members 330 and upper end portions thereof are rotatably connected with lower end portions of the cam levers 329 through a hole 333 formed in the plate member 327, such that they are rotatable about pins 332, respectively.

The hook members 330 are inwardly biased to each other by springs 334 as shown in FIG. 5A so that the right side cam lever 329, for example, is biased counterclockwise direction. In order to maintain the hook members 330 in the position shown in FIG. 5A, the clockwise movement of the cam levers 329 is limited by stoppers 335, respectively.

When the slider member 323 is lowered with rotation of the motor 324' the hook members 330 are lowered to with the position shown in FIG. 5A. When the slider member 323 is lowered beyond a level in which the lower ends of the cam levers 329 contact with the lower edge of the frame 321, the lower end portions of the cam levers 329 are moved inwardly by the lower edge of the frame 321. Therefore, the hook members 330 are rotated away from each other to open the hooks 330a against the biasing force by the spring 334. Therefore, the cartridge 4 can be grasped thereby as shown in FIG. 5B. Then, when the slider member 323 is moved up, the cartridge 4 is lifted up by the hooks 330a stably with an aid of the spring 334.

The pick-up device 33 holding the cartridge 4 in this manner is moved by the crane mechanism to the predetermined position A shown in FIG. 3 and then the pick-up device 33 is lowered again so that the cartridge 4 can be unhooked by a contact of the lower ends of the cam levers 329 with the lower edge of the frame 321. Thereafter, the pick-up device 33 is returned to a next position of the cartridge stocker 31.

Lift Mechanism

The lift mechanism 32 moves the cartridge 4 transported by the crane mechanism in the lower level up to an upper level and then onto a reaction line. Therefore, the lift mechanism 32 is arranged at the position A.

Figures 6A, 6B:
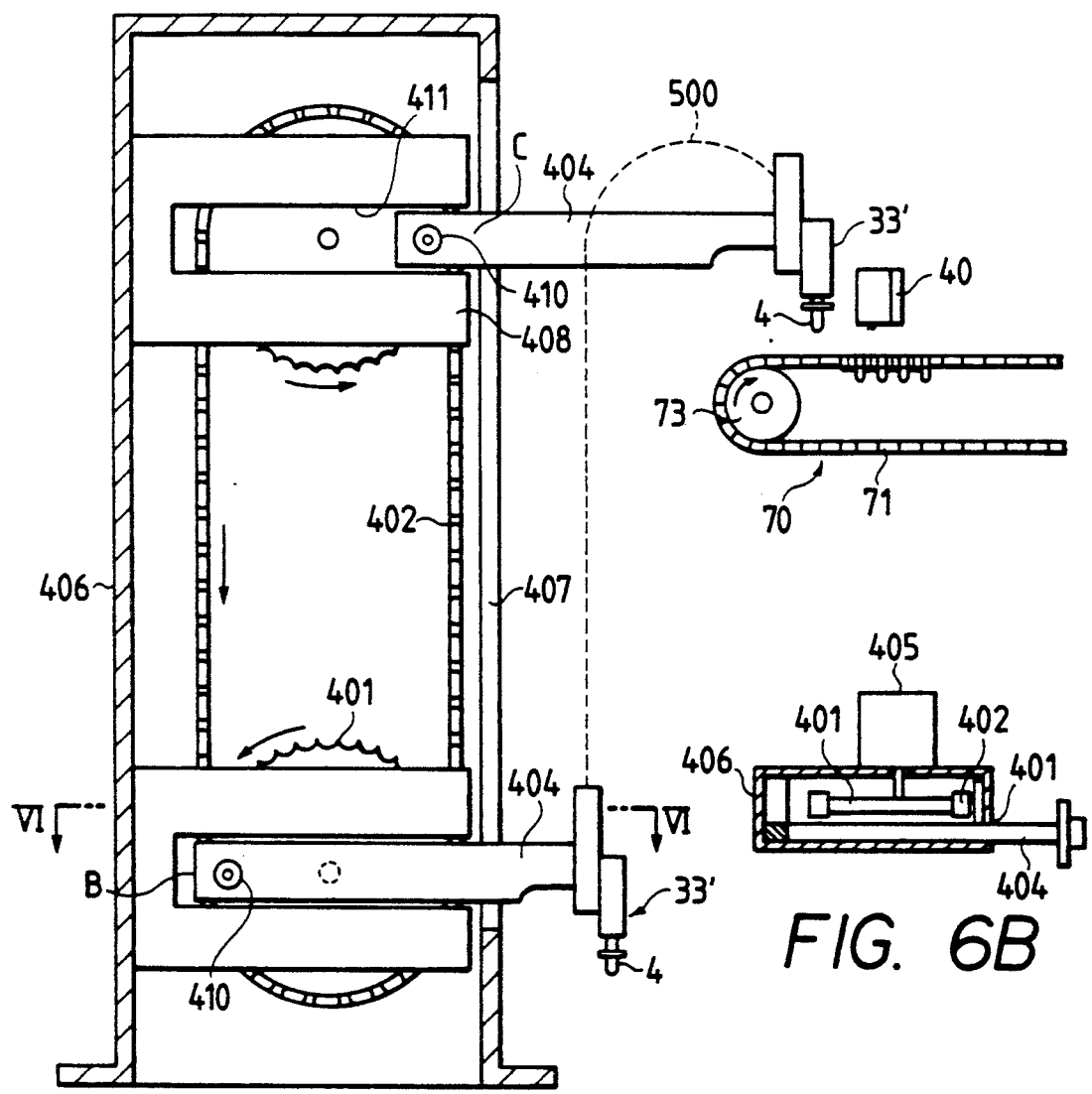
FIG. 6A is a cross section of a lift mechanism.
FIG. 6B is a cross section taken along a line VI—VI in FIG. 6A.

FIG. 6A and FIG. 6B which is a cross section taken along a line VI—VI in FIG. 6A show the lift mechanism 32. In FIGS. 6A and 6B, the lift mechanism 32 includes an upright frame 406 having a vertical slot 407 in its front wall, a reversible motor 405 (FIG. 6B) disposed outside the frame 406 and a pair of vertically arranged sprockets 401 fixedly disposed in the frame 406. Either one of the sprockets 401 is connected to a shaft of the reversible motor 405 so that a chain 402 can be driven reversibly on the sprockets 401 thereby within a limited range as shown in FIG. 6A. A slider block 408 is housed in the frame 406 slidably vertically and has a lateral slot 411 opened to the front wall of the frame 406. An arm 404 is slidably received in the lateral slot 411. A rear end portion of the lateral arm 404 is rotatably connected to a position 410 on the chain 402 such that, when the slider block 408 is in the lowest position in the frame 406, the arm 404 is fully retracted and, after it passes the highest position in the frame, the arm is fully retracted as shown in FIG. 6A. In detail, a front portion of the arm 404 extends over the frame 406 through the vertical slot 407 thereof and is equipped with a pick-up device 33' similar to the pick-up device 33 of the transportation mechanism. The reversible motor 405 drives the sprocket reversibly to reciprocate the chain 402 within a range defined between positions B and C of the connecting point 410 of the rear end of the lateral arm 404 and the chain 402 such that the front end of the arm 404 moves along a locus shown by a dotted line 500 in FIG. 6A. That is, in FIG. 6A, the fully retracted arm 404 is moved by rotation of the sprocket 401 in the arrow direction up to the position of the upper sprocket 401. Then, after passing along an upper quarter circle of the upper sprocket 401, the lateral arm 404 is moved down while being protruded gradually and, finally, it is fully extended at the end of a subsequent quarter circle movement of the sprocket.

The semi-circle locus of the upper end portion of the movement of the front end of the lateral arm 404 and hence the pick-up device 33' is important for the stable shift of the cartridge onto the reaction line 11.

The catching and releasing operation of the pick-up device 33' with respect to the cartridge 4 is the same as that mentioned with respect to FIGS. 5A and 5B. That is, at the lower position of the arm 404, the slide member is lowered to catch the cartridge and then moved up. Then, the device 33' is moved together with the arm 404 along the dotted locus 500 and, at the end of the locus 500, the slider member is lowered again to release the cartridge onto the reaction line 11.

XII Construction of Upper Level

Sampler Portion

As shown in FIG. 3, a sampling chip cassette 12 and a sample cassette 13 are arranged in a second, upper level. The sampling chip cassette 12 includes a plurality of sampling chips 44 arranged in a horizontal plane and the sample cassette 13 includes a plurality of sample containers 13a, each containing a sample liquid containing substance to be measured, arranged in a plane.

Reaction Line 11

The reaction line 11 extends generally in a direction perpendicular to the inserting direction of the cartridge stocker 31 in the lower level. The reaction line 11 is composed of a pair of parallel endless belts 71 as shown in FIG. 2 and 3. The endless belts 71 support the opposite end portions of each cartridge 4, respectively, so that the cartridge can be stably moved therealong. The endless belts 71 are driven by sprockets 72 arranged in opposite end portions of the reaction line 11, which are in turn driven by stepping motors, such that the cartridge put on the reaction line can be stepped with an interval of, for example, 30 seconds.

The cartridge 4 lifted up by the lift mechanism 32 and put on a starting portion of the reaction line 11 is stepped to a next position on the reaction line 11 after 30 seconds and this is repeated until a measurement therefor is completed. There are several devices arranged along the reaction line 11, which are necessary to provide a required reaction. Such devices will be described in detail later.

Seal Breaker

As mentioned previously, the cartridge 4 put on the starting point on the reaction line 11 has the wells sealed by the sealing film 11f. In order to remove such seal, a seal breaker 40 is provided above the reaction line 11 at a position next to the starting position. In the shown embodiment, the seal breaker takes the form of a block having a lower surface formed with a plurality (in this case, three) of downward protrusions so that, by lowering the block, portions of the sealing film 10f on the respective wells of the cartridge are broken by the protrusions to make the wells accessible. Since the design of such block is arbitrary and those skilled in the art can design it easily, the details thereof are not shown here.

Sample Crane Mechanism

As shown in FIGS. 2 to 4, a sample transportation mechanism is provided above the upper level, which has substantially the same construction as that of the cartridge transportation mechanism except that a sampling pump unit 82 is mounted on an arm 81 instead of the pick-up device 33. In detail, the sampling crane mechanism includes a pair of rails 80, the arm 81 slidable along the rails 80 and the sampling unit 82 mounted on the arm 81 movably therealong. The movement of the pump unit 82 in a plane is substantially the same as that of the pick-up device 33.

Sampling Pump Unit

Figure 7:
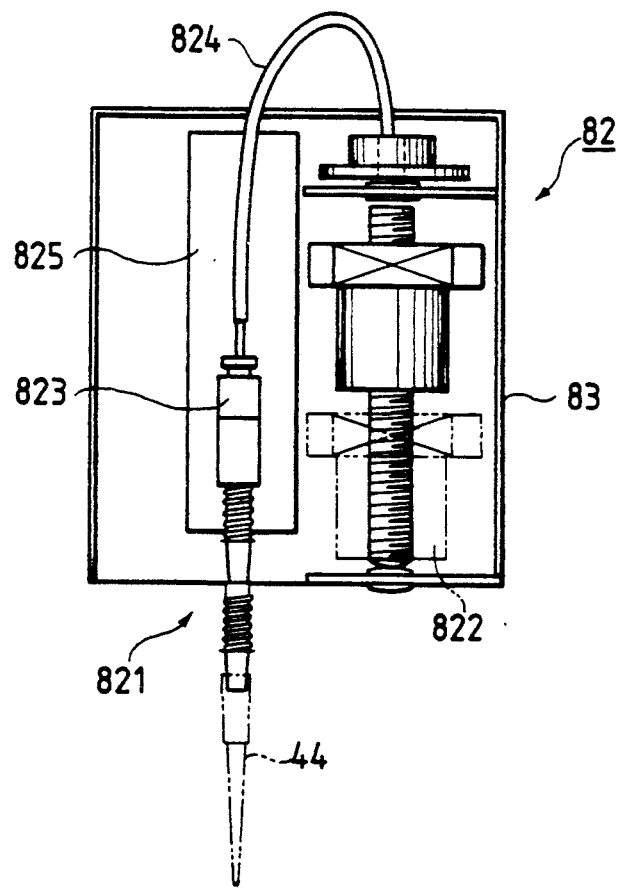
FIG. 7 shows a construction of the pouring device for pouring desired solution to a required well of the cartridge through a chip picked up thereby.

The sampling unit 82 shown in FIG. 7 includes a nozzle portion 821 and a pump portion 822 both arranged within a case 83 and connected to each other by a suitable tube 824. The nozzle portion 821 includes a nozzle 823 which is fixedly secured to a plate 825 which is movable vertically by means of a solenoid, for example. When the nozzle 823 is lowered, a top end thereof engages a chip 44 in the sampling chip cassette 12. Then, it is lifted up and moved to bring the chip 44 to a suitable location at which the pump portion 822 is actuated to aspirate a liquid contained therein and then moved another location to pour it thereto. Thereafter, it is moved to a location d (FIG. 3) to dispose the used chip into the chip disposer 700.

Stirring Portion and B/F Separator

Figure 8:
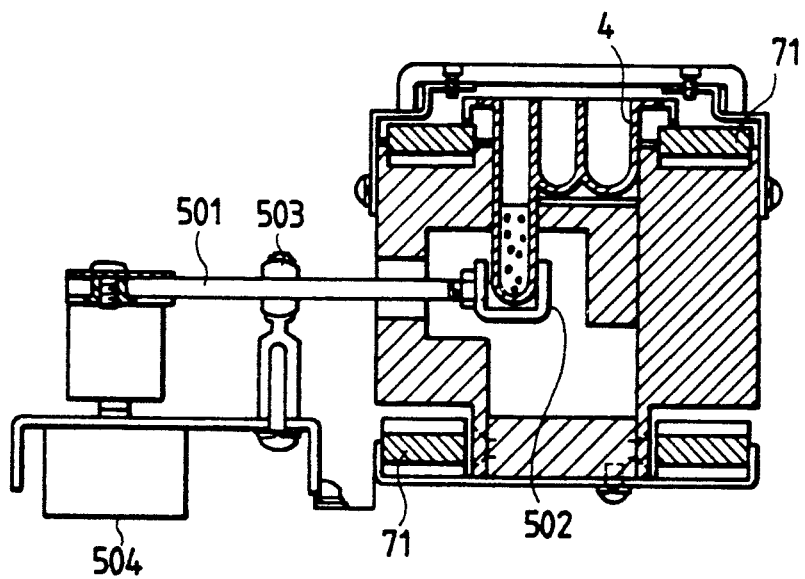
FIG. 8 is a cross sectional view of a stirring portion.
Figure 9:
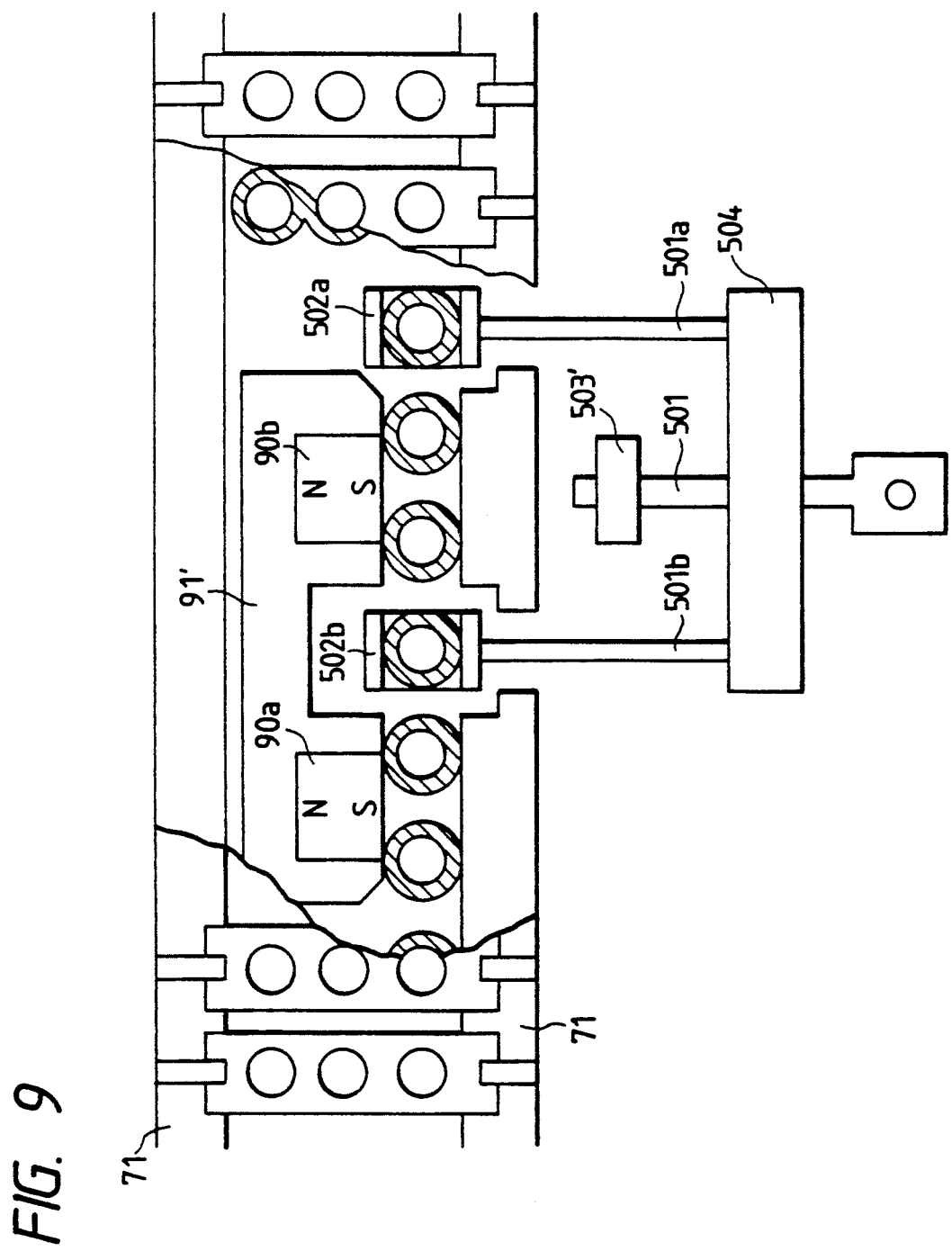
FIG. 9 shows another modification of the B/F separator together with a B/F separator; shown in FIG. 9.

FIGS. 8 and 9 show an example of the stirring portion. In FIG. 8, which is a cross section of the stirring portion, a bar 501 has one end connected eccentrically to a shaft of a motor 504 and the other end mounting a U shaped member 502. A middle portion of the bar 501 is elastically supported by a support 503. The U shaped member 502 is adapted to fittingly receive the first well of the cartridge 4 transported by the endless belts 71. Upon rotation of the motor 504, the bar 501 is vibratingly driven thereby to vibrate the U shaped member 502 so that the first well received therein is vibrated to stir the content thereof. In FIG. 9 which is a plan view of a modification of the stirring portion shown in FIG. 8, a lateral beam 504 is fixedly secured to a middle portion of a bar 501 having one end eccentrically connected to a motor shaft and the other end elastically supported by a support member 503'. From opposite end portions of the lateral beam 504 a pair of bars 501a and 501b extend. Ends of the bars 501a and 501b mount U shaped members 502a and 502b, respectively. Between the U shaped members, a magnetic B/F separator 90 (FIG. 10) is disposed.

Figure 10:
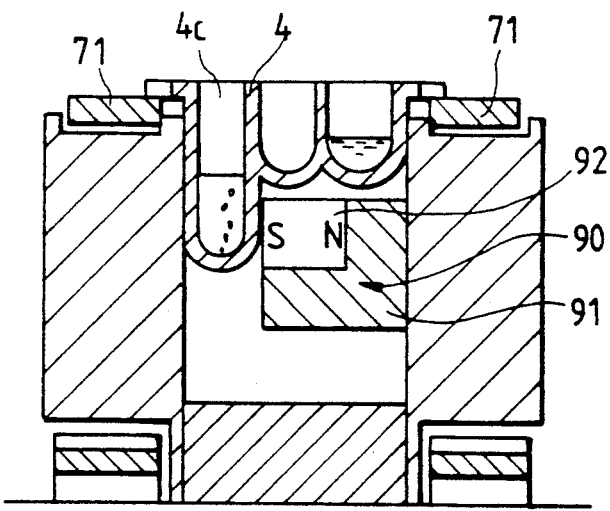
FIG. 10 is a cross section of the B/F separator shown in FIG. 9.

The B/F separator 90 includes a permanent magnet 92 supported by a magnetic member 91 arranged in one side of a passage of the first well of the cartridge 4 as shown in FIG. 10. By passing the magnet 92, magnetic particles contained therein are attracted to the wall of the cartridge well and, by washing the well with suitable washing liquid, free antigen or antibody can be removed.

Figure 11:
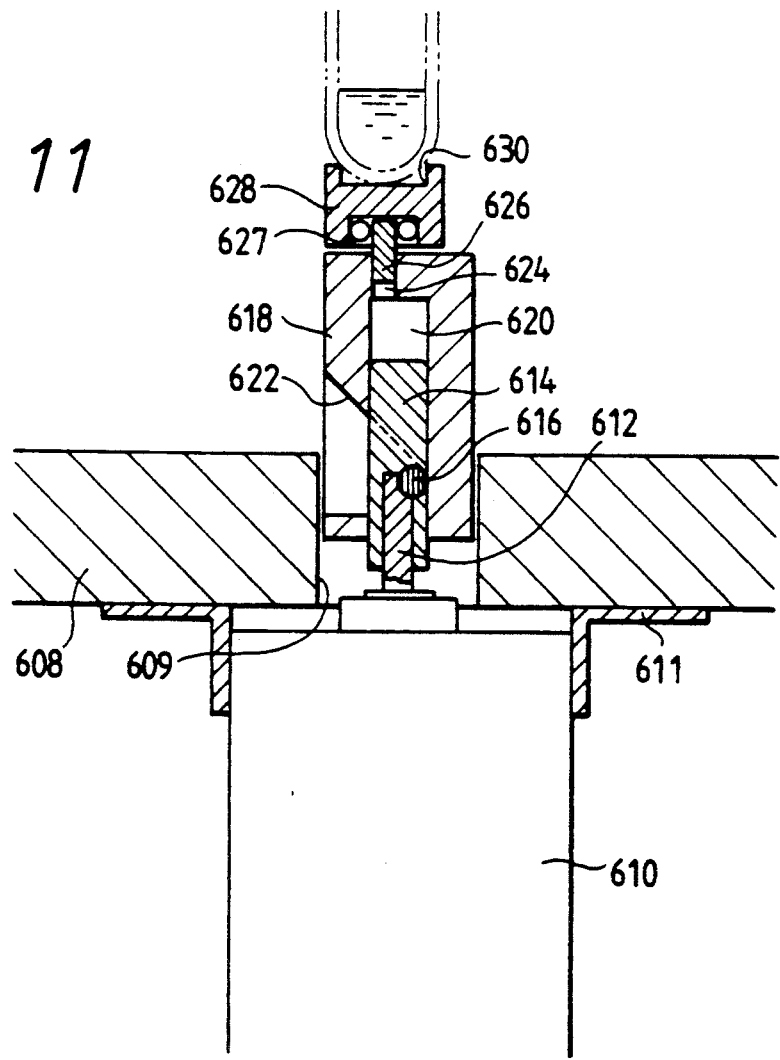
FIG. 11 is a cross section showing another embodiment of the stirring portion.

FIG. 11 shows another example of the stirring portion. In this example, a generally cylindrical member 618 of material whose specific weight is relatively large has a blind hole 620 and a cam slope 622 is formed in a wall of the cylinder by cutting. A plug member 614 is inserted into the blind hole 620. The plug member 614 has a blind hole into which a shaft of an upright motor 610 is fixedly inserted. The plug 614 has a protrusion 616 which follows the cam slope. In the bottom of the blind hole 620 of the cylinder 618, an eccentric hole 624 is formed into which a pin 626 is fixedly inserted. A well receiver member 628 is rotatably supported by an exposed portion of the pin 626 through a bearing 627. The well receiver member 628 has a recess 630 thereon in which the well is received. Due to the weight, the cylinder member 618 tends to go down by gravity. Therefore, when out of operation, it is fully lowered such that the protrusion 616 of the plug 614 contacts with the uppermost position on the cam slope 622. When the motor 610 rotates counterclockwise direction, the plug 614 is rotated counterclockwise direction, so that the pin 616 thereof pushes the cylinder 618 up along the cam slope 622. When the cylinder 618 reaches the uppermost position at which the well receiver 628 receives the well, the cylinder 618 rotates in a counterclockwise direction while keeping the positional relation to the well as it is. Since the well receiver 628 is slightly eccentric with respect to the cylinder 618, the receiver 628 is vibratingly rotated, so that the content of the well is stirred.

Figure 12:
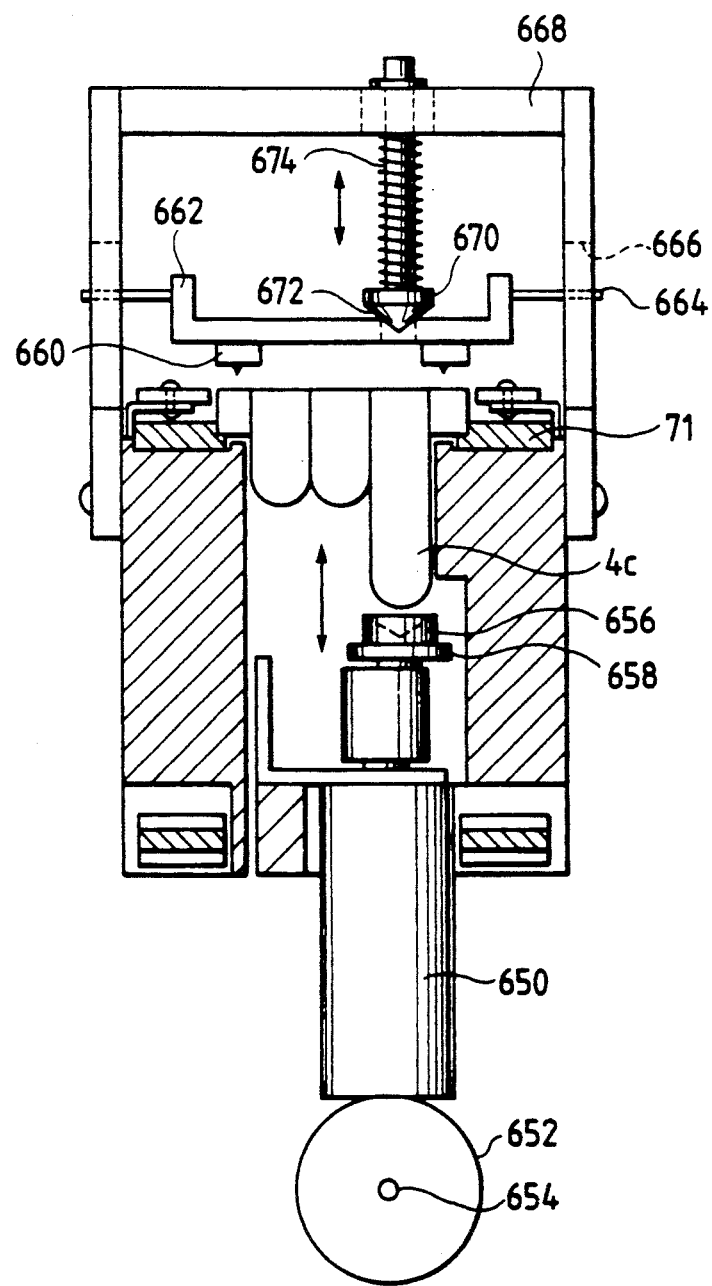
FIG. 12 shows a still another embodiment of the stirrig portion.

FIG. 12 shows another example of the stirring portion. In FIG. 12, an upright motor 650 is arranged between the endless belts 71 in such a manner that it can be moved vertically by, for example, a cam member 652 mounted on a lateral shaft 654 and in contact with a bottom of the motor 650. On a shaft of the motor, a well receiver 656 is eccentrically mounted rotatably through a bearing 658. In the upper position of the motor, the well receiver can receive a bottom portion of the cartridge well 4c carried by the belts 71 and, upon a further upward movement of the motor, the well receiver pushes the cartridge up.

When the cartridge is substantially pushed up, it abuts cartridge guides 660 formed on a lower surface of a holder member 662 at positions corresponding to the notches of the cartridge. A vertically movable range of the holder member is limited by engagements of lateral pins 664 thereof with vertical slots 666 formed in a generally reversed-U shape frame 668. Between the holder and the top portion of the frame, a fulcrum member 670 is provided, which has a pointed lower end which is received in a hole or recess 672 formed in the upper surface of the holder member. The fulcrum member is biased downwardly by a spring 674 to thereby bias the holder member down.

When the motor is moved up to the uppermost position by the cam member, it is energized to eccentrically rotate the well receiver to thereby stir the content of the well. In this case, since the holder member holds the upper portion of the cartridge stationarily, the eccentric vibrating movement of the well receiver can be efficiently transmitted to the well, resulting in sufficient stirring.

When a plurality of such stirring portions are arranged along the reaction line, the vertical movements of motors 650 thereof may be controlled by identical cam members to that (652) mounted on the same shaft at different angles, respectively.

Measuring Portion

Figure 13:
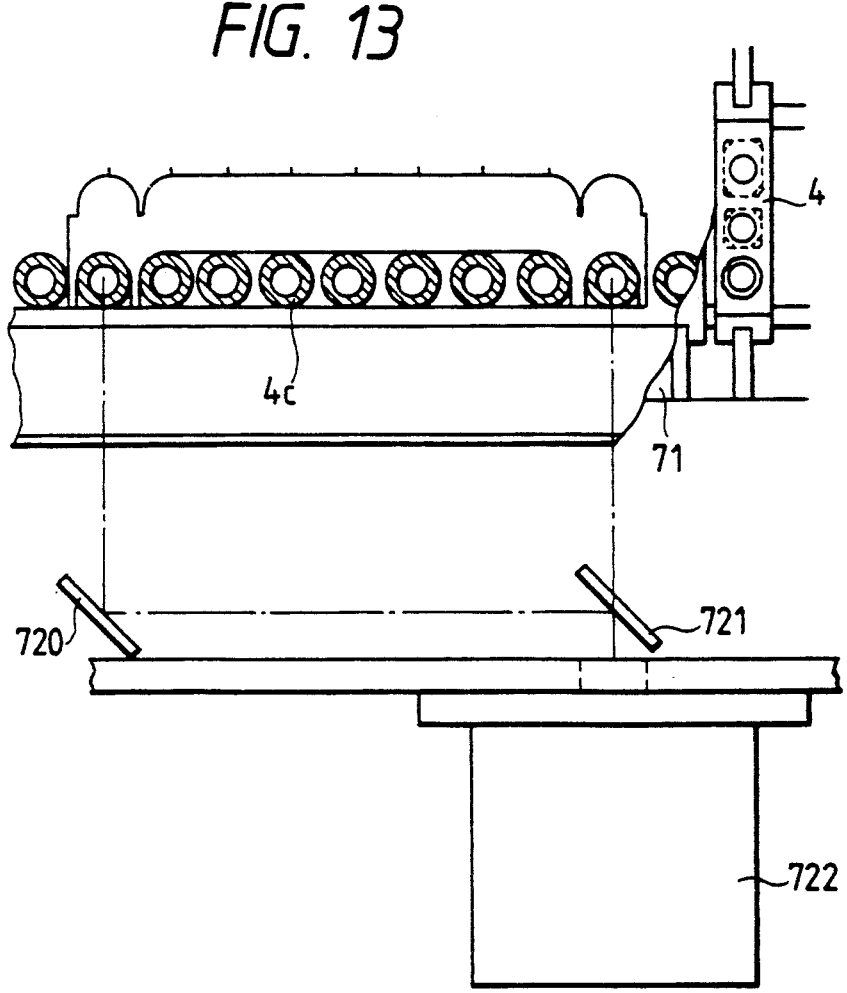
FIG. 13 shows an embodiment of the optical measuring portion.

FIG. 13 shows an example of the measuring portion 20. This is to measure luminance of enzyme bound with magnetic particle carrying antigen or antibody at a specific wavelength. It includes a reflection mirror 720, a partial reflection mirror 721 and a photomultiplier 722. In this example, luminance at a time is measured by the photomultiplier 722 through the reflection mirror 720 and the partial reflection mirror 721 and luminance at a later time is measured through the partial reflection mirror 721 directly. A revolver may be associated therewith to remove error due to abnormal reflection light, if necessary.

Figure 14:
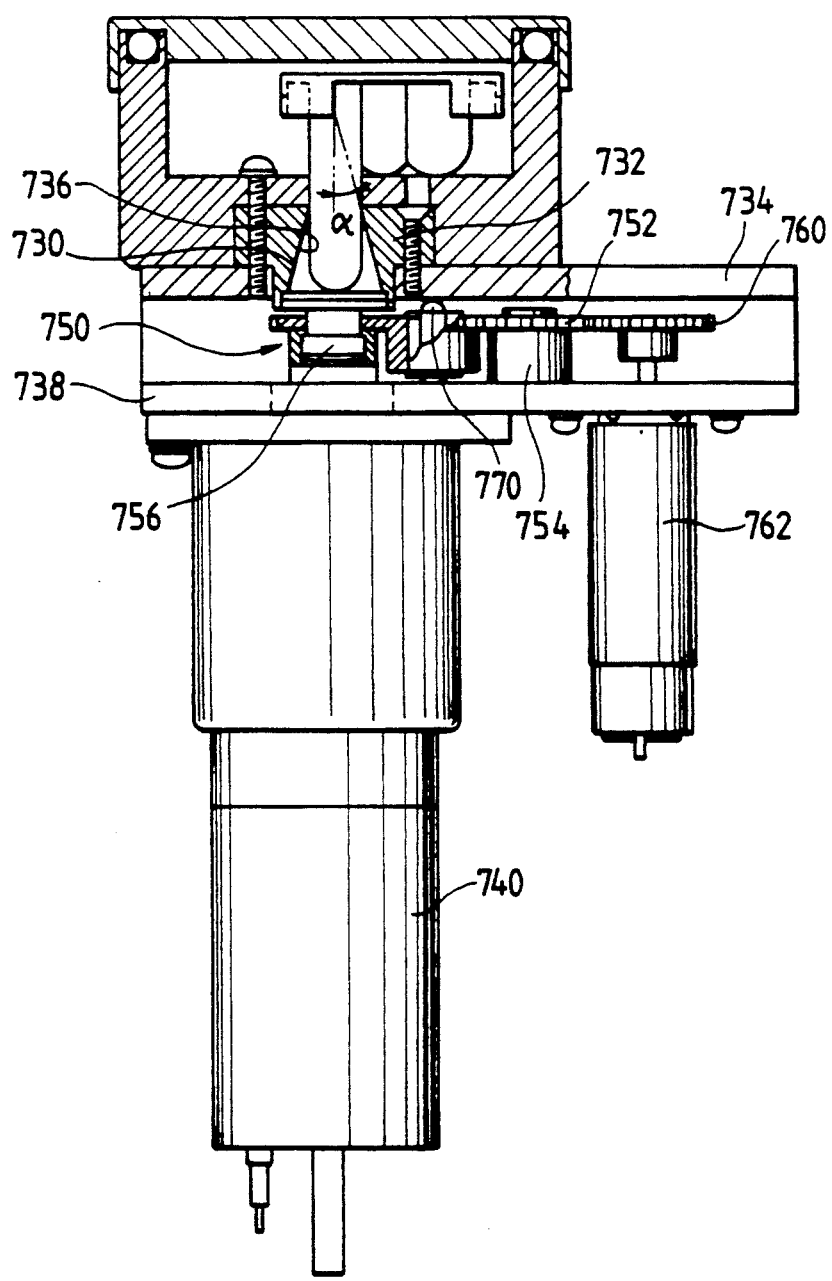
FIG. 14 shows another embodiment of the optical measuring portion.

FIG. 14 shows another example of the measuring portion. In FIG. 14, the first well 4c of the cartridge 4 in which the desired reaction is to be measured is received in an upper opening of an optical reflective cylinder 730 in the form of a downwardly diverging hole formed in a block member 732 provided on a hole formed in a first deck 734, with an upper diameter thereof being substantially the same as that of the well 4c. An angle α of a taper wall 736 of the cylinder 730 may be within a range from 10° to 60°. However, it has been found that a satisfactory result is obtained when the angle α is about 30°.

A second deck 738 is provided below the deck 734 in parallel to each other. The second deck 738 has a hole corresponding, in position and size, to the hole of the first deck 734. A photo multiplier 740 is arranged correspondingly to the cylinder 730 below the hole of the second deck 738 by a suitable means.

A filter 750 is disposed between the first deck and the second deck. The filter 750 includes a disc 752 rotatably supported by a pin 754 supported between the decks. The disc 752 has a plurality of holes formed along a peripheral portion thereof in each of the holes a filter member 756 is disposed.

Figure 15:
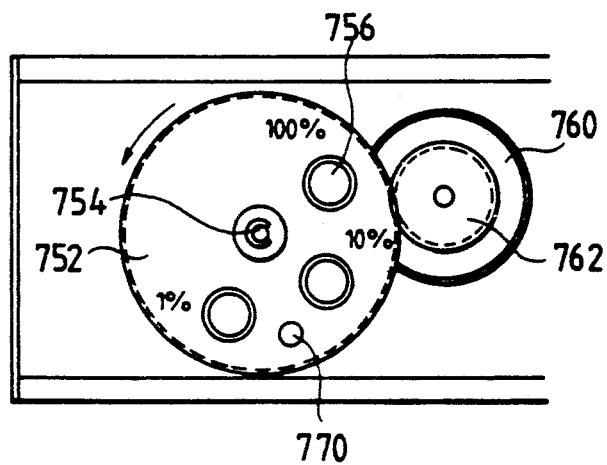
FIG. 15 is a plan view of the optical measuring portion shown in FIG. 14.

The peripheral edge of the disc is geared to mesh with a gear 760 mounted on a shaft of a motor 762 so that the disc 752 is rotated by the motor 762 to put a desired filter member 756 exactly in the position between the cylinder 730 and the photo multiplier 740. FIG. 15 shows the relative positions of the disc 752, the motor 762 and the gear 760.

Three filter members 756 are provided in the shown embodiment, which have transparencies of 1%, 10% and 100%, respectively. The number of the filter members and their transparencies can be selected arbitrarily on demand.

A position sensor 770 is provided on the disc 752 to detect a rotational angle of the disc. The sensor 770 may be a magnetic sensor. According to an output of the sensor 770, the motor 762 is controlled to position a desired filter member in place.

Figure 16:
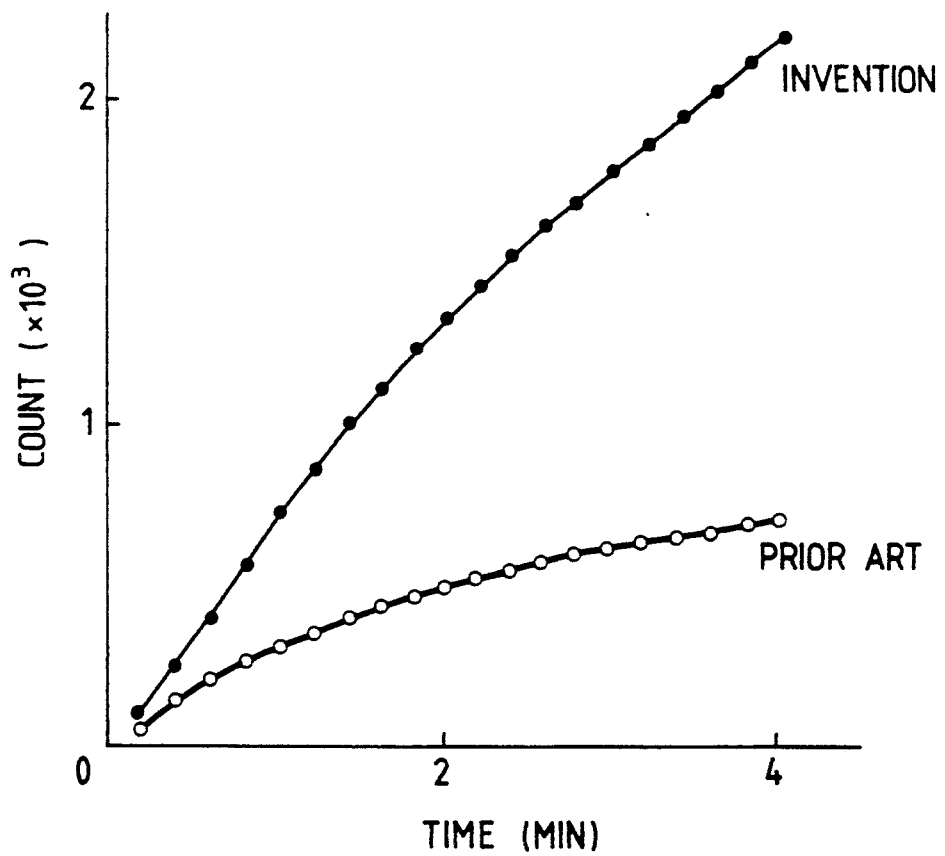
FIG. 16 is a graph showing an effect of the measuring portion shown in FIG. 14.

The taper wall 736 of the cylinder 730 is important as mentioned previously. FIG. 16 shows the result of an experiment conducted to clarify the effect of the taper cylinder. In this experiment, luminance of a mixture of 0.1 M tris buffer solution (pH9.8), 20 $\mu$l of alkaliphosphatase (1 $\mu$g/ml) and 300 $\mu$l of AMPPD is measured with and without the cylinder 730 having a taper angle of 30°.

Cartridge Disposer

Figure 17:
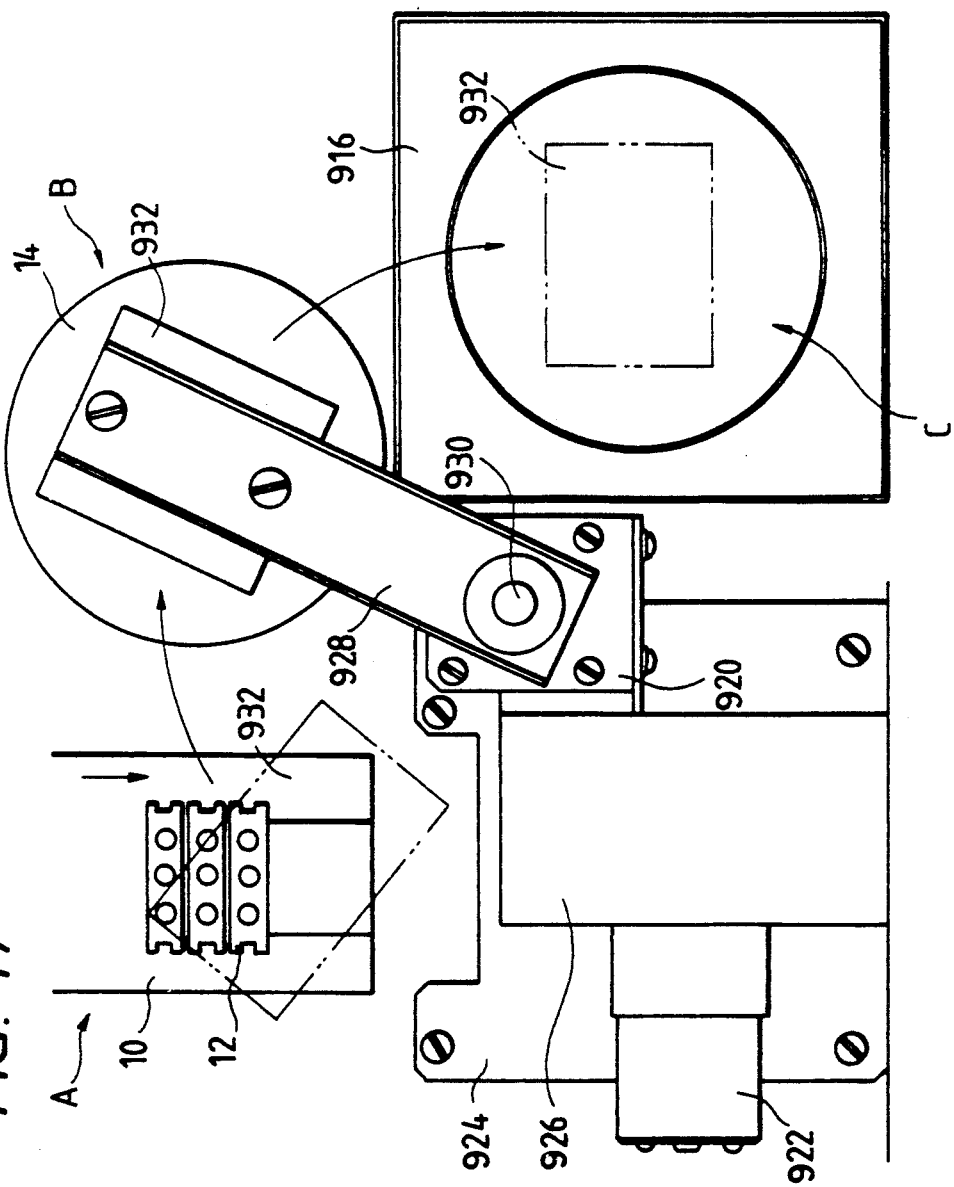
FIG. 17 is a plane view of a cartridge disposer.
Figure 18:
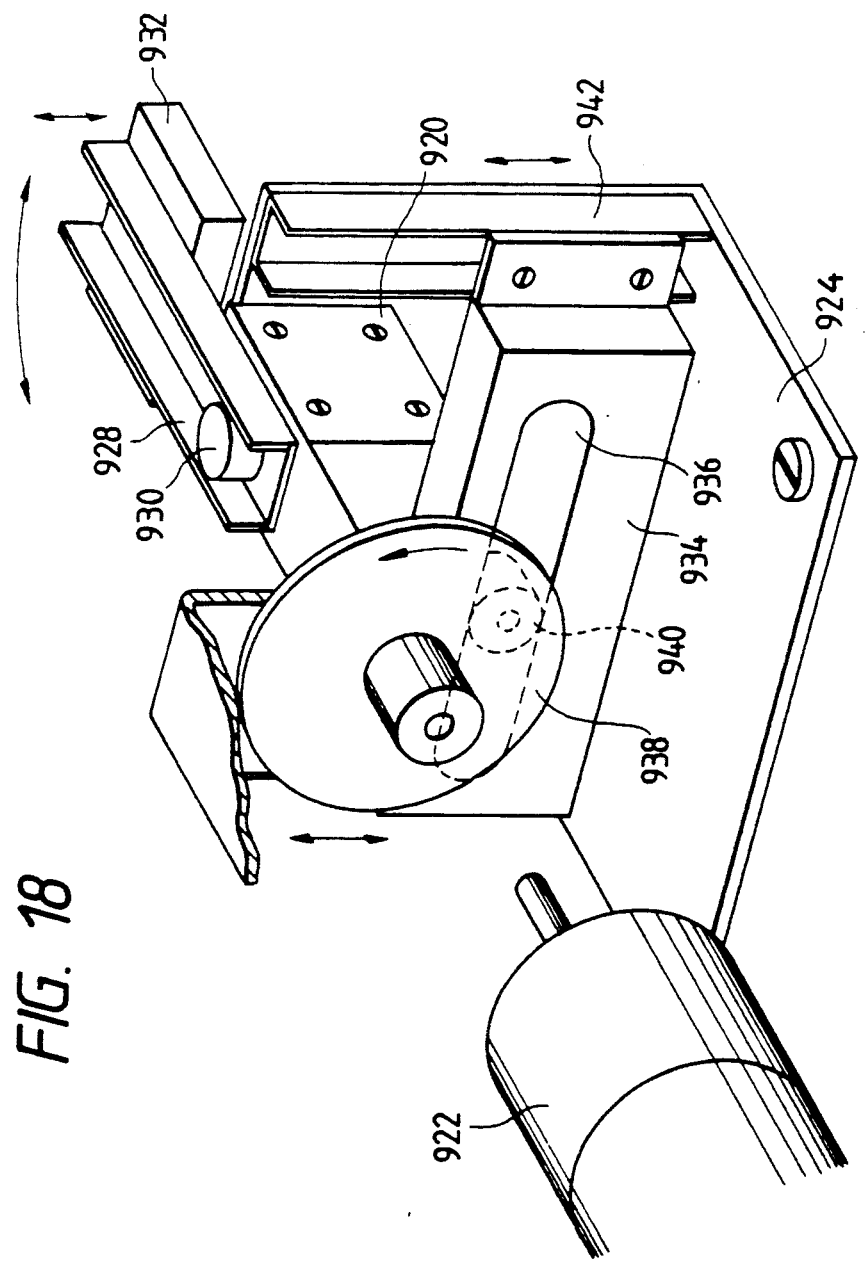
FIG. 18 is a perspective view of the cartridge disposer.

FIG. 17 is a plan view of the cartridge disposer and FIG. 18 is a perspective view of the cartridge disposer 21 shown in FIG. 2. In FIGS. 17 and 18, the cartridge disposer 21 is disposed at an end portion of the reaction line 11 at which the cartridges 4, the measurements of which are completed, arrive one by one. The disposer includes an arm elevation device 926 mounted on a base 924. The elevator device includes a pair of vertical rails 942, a cam block 934 supported vertically slidably by the rails, a d.c. motor 922 having a shaft supporting a disc 938 provided on its periphery with a roller 940 which engages with a cam slot 936 formed horizontally in the cam block 934, a block 920 fixedly secured to the cam block 934 and housing a stepping motor, an arm 928 having one end fixedly connected to a shaft 930 of the stepping motor and a pick-up device 932 mounted on the other end of the arm 928.

The pick-up device 932 may have substantially the same construction as that of the pick-up device 33 of the cartridge crane mechanism, with some parts being removed.

In operation, the cam block 934 is lifted along the rails 942 by a rotation of the motor 922 through the disc 938, the engagement of the roller 940 thereof with the cam slot 936. Then, the stepping motor of the block 920 is actuated when a cartridge arrives at the end of the reaction line to bring the other end of the arm 928 and hence the pick-up device 932 above the arrived cartridge. Thereafter, the cam block 934 is lowered onto the cartridge so that the pick-up device 932 can engage the cartridge in the same manner as mentioned with respect to the pick-up device 33 of the cartridge transportation mechanism. Then, the cam block is lifted again and the arm 928 is rotated in reverse direction above the disposer container 916. At this position, the pick-up device 932 is actuated to release the cartridge to allow it to drop into the container. This sequence of operations is repeated for each cartridge arriving.

FIGS. 19 to 22 show flowcharts of the one-step method, the two-step method, the delay method and the two-step method with dilution, to be performed by the present apparatus, respectively. In these flowcharts, the steps S1 and S2 are common for all of these methods. In step S1, an operator actuates the start button 2a of the input portion 2 so that the transportation of the cartridges in the cartridge stocker is started one by one to the start position on the reaction line through the cartridge crane mechanism and the cartridge lift mechanism and to break the seal of the cartridges on the reaction line successively through the seal breaker (step S2). Then the operator operates the selection button 2b thereof to select a program corresponding to a reaction to be obtained. The CPU 24 reads out the selected program from the program memory and starts to control the operation of the various portions of the apparatus so that the selected program can be performed.

Figure 19:
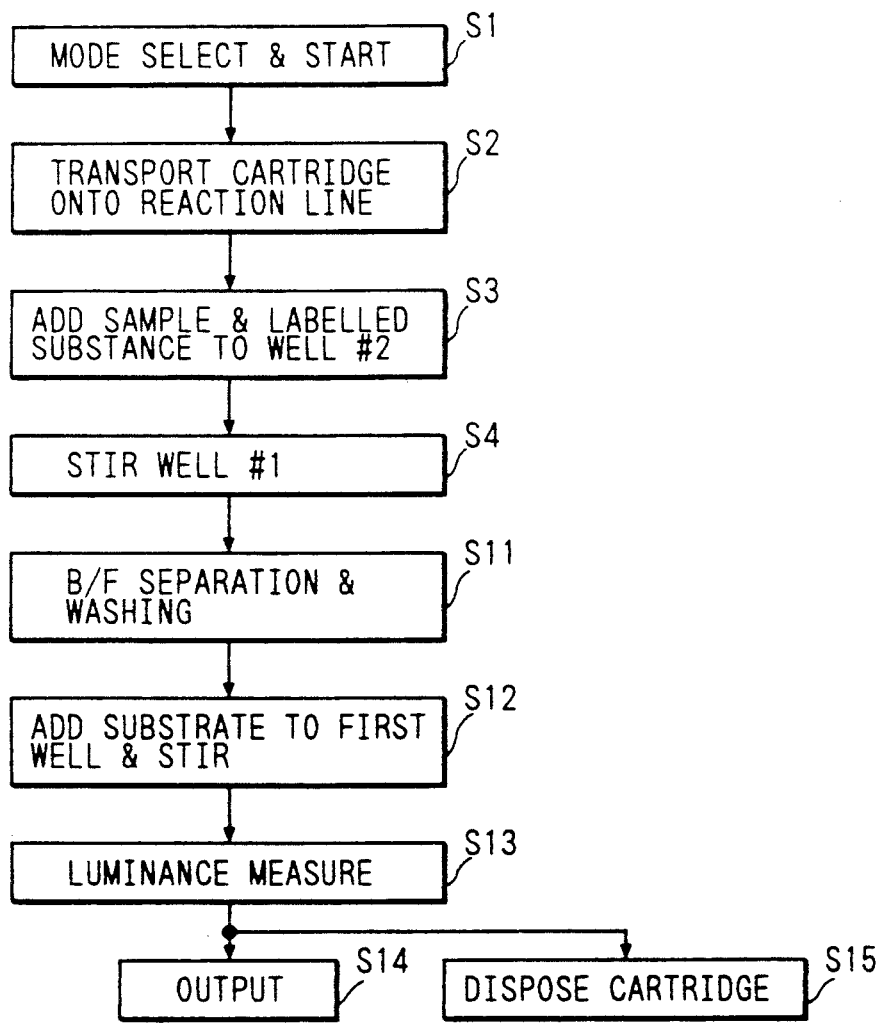
FIG. 19 is a flowchart showing the one step immunoassay method to be performed using the apparatus according to the present invention.

In FIG. 19 which shows the one step method mentioned above, the sampling crane mechanism and the aspirating/pouring portion are actuated to pick up a chip into which a sample is taken in by aspiration and poured into a first well of the cartridge, which contains magnetic particles carrying antigen or antibody, and, after the chip is disposed, to pick up another chip into which enzyme labelled substance contained in a second well of the cartridge is taken in and poured to the first well (step S3). Then, the first stirring portion 17a is activated to stir the mixture in the first well of the cartridge moved to a next position on the reaction line 70 (step S4). Then, when the cartridge reaches a first magnetic B/F separator 18a, a B/F separation is performed, followed by washing by means of a first washing portion 19a (Step S11). Then, substrate is added to the first well by the substrate pouring portion 16c and stirred in the second stirring portion 17b (Step S12). Then, an optical measurement is performed by the measuring portion 20 (Step S13) and an output thereof is supplied to the CPU 24 (Step S14). At the same time, the cartridge is disposed by the disposer portion (Step S15).

Figure 20:
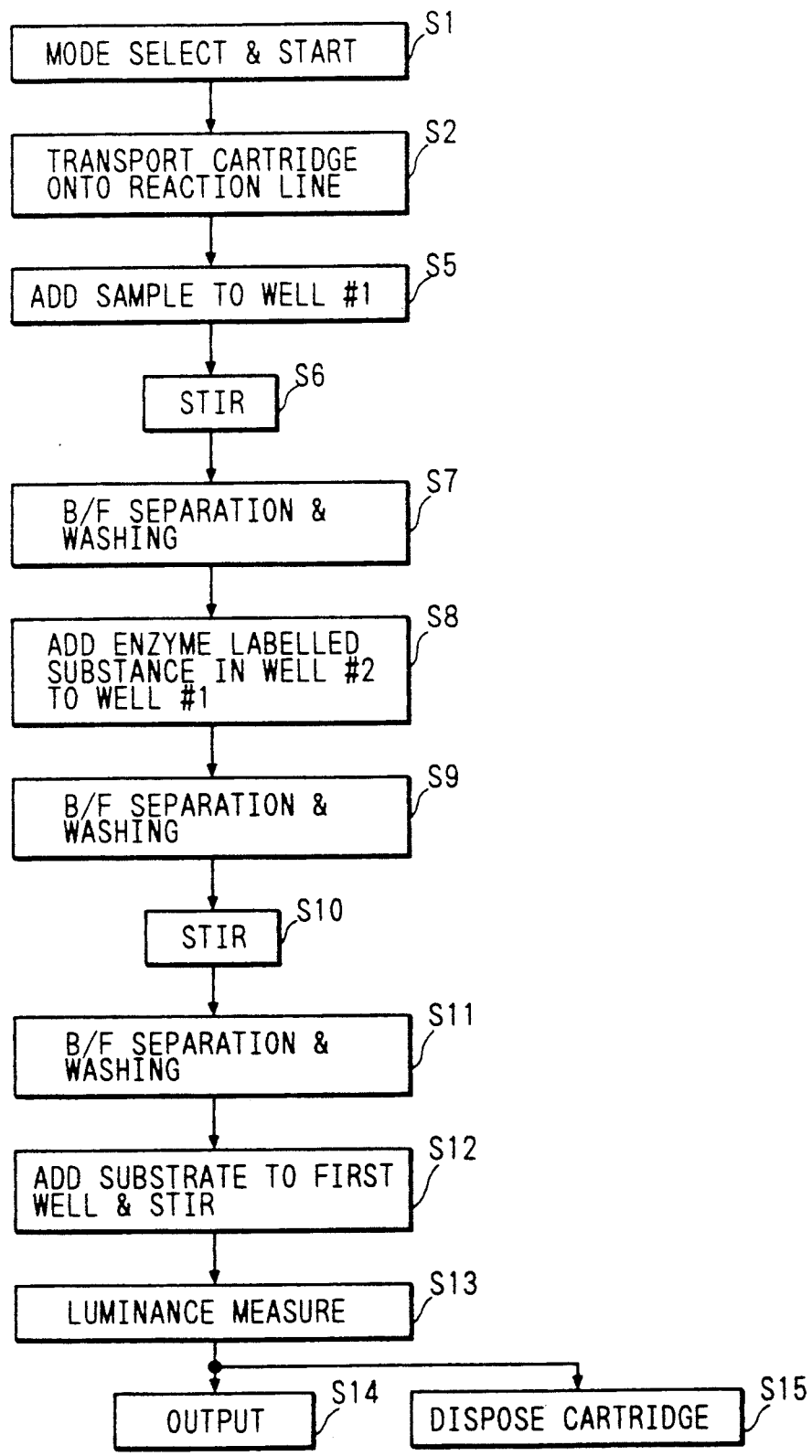
FIG. 20 is a flowchart showing the two step immunoassay method to be performed using the apparatus according to the present invention.

FIG. 20 shows the two step method mentioned above. After the step S2, a sample is poured to a first well of the cartridge, which contains magnetic particles carrying antigen or antibody (Step S5). Then, the first stirring portion 17a is activated to stir the mixture in the first well of the cartridge moved to a next position on the reaction line 70 (step S6). Then, when the cartridge reaches a first magnetic B/F separator 18a, a B/F separation is performed, followed by washing by means of a first washing portion 19a (Step S7). Then, enzyme labelled substance contained in a second well of the cartridge is poured to the first well and stirred (Step S8). Thereafter, a magnetic B/F separation and washing are performed in the Step S9. Then, after stirred again in Step S10, substrate is added to the first well by the substrate pouring portion 16c and stirred in the second stirring portion 17b (Step S12). Then, an optical measurement is performed by the measuring portion 20 (Step S13) and an output thereof is supplied to the CPU 24 (Step S14). At the same time, the cartridge is disposed by the disposer portion (Step S15).

Figure 21:
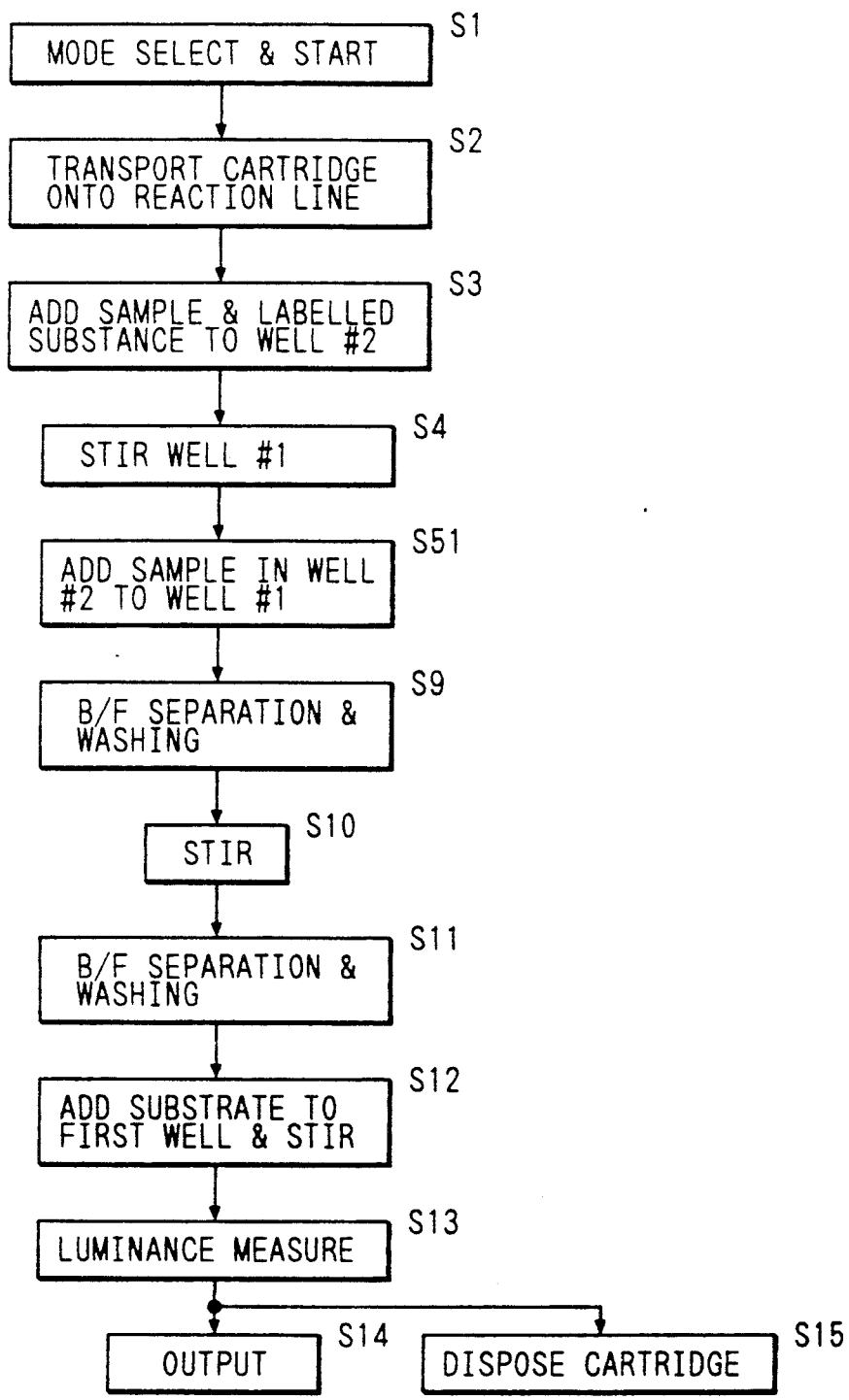
FIG. 21 is a flowchart showing the delayed immunoassay method to be performed using the apparatus according to the present invention.

FIG. 21 shows the delay method using dilution mentioned above in which the steps S1 to S4 are the same as those in FIG. 18. After the step S4, magnetic particles carrying antigen or antibody contained in a first well of the cartridge are mixed with a sample and enzyme labelled substance and the mixture is stirred by the first stirring portion (Step S51). Then, the Steps S9 to S15 are performed with respect thereto as in the steps shown in FIG. 20.

Figure 22:
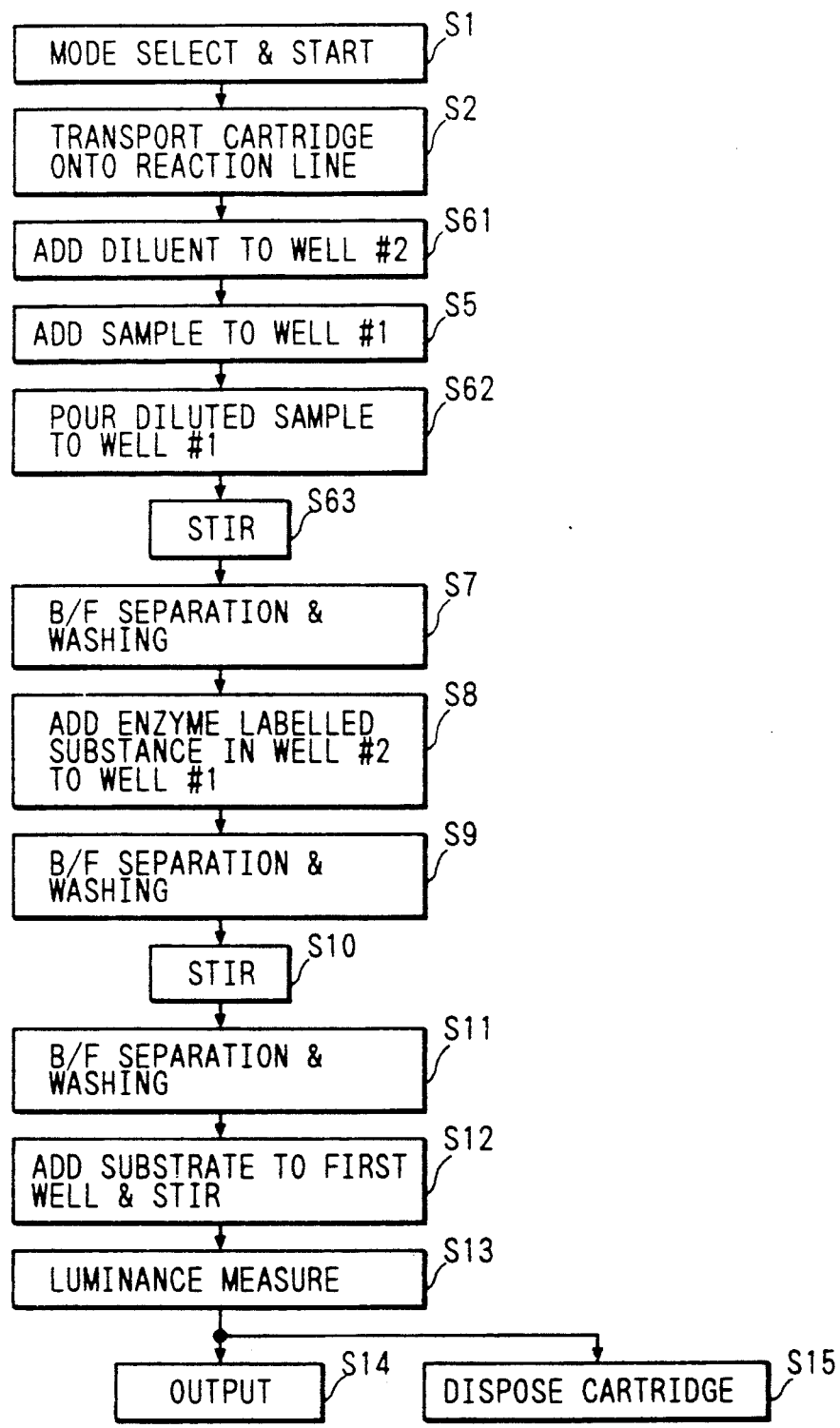
FIG. 22 is a flowchart showing the two step immunoassay method using diluent, to be performed using the apparatus according to the present invention.

FIG. 22 shows the two step method using diluent. In FIG. 22, after the step S2, diluent is poured to a first well of the cartridge from the diluting portion 25 (Step S61) and a sample is poured to the same well (Step S5). The resultant diluted sample is poured to a second well containing magnetic particles carrying antigen or antibody (Step S62). Then, after being stirred by the first stirring portion 17a (Step S63), a B/F separation and washing are performed in Step S7. Thereafter, the same steps 8 to 15 are performed as in the two step method shown in FIG. 20.

As described hereinbefore, according to the present invention, a sequence of operations necessary to perform an immunoassay measurement can be completely automated by the use of the cartridges each having at least two wells, at least one of which contains solid phase material, and the reaction line for steppingly moving these cartridges one by one while performing necessary operations with respect to the cartridges by means of at least one B/F separator, at least one stirrer, at least one pouring portion, at least one washing portion, an optical measuring portion, etc., arranged along the reaction line in a suitable order. The cartridges described may be modified respectively to accommodate desired applications. The constitutional components of the present apparatus can be also modified suitably. Such modifications fall in the scope of the present invention.

What is claimed is:

1. An automatic immunoassay apparatus comprising a sample stocker portion for storing a plurality of samples, a reagent stocker for storing washing solution and diluent, a plurality of reaction cartridges each having at least two wells, a first well of said at least two wells containing solid phase material carrying antigen or antibody, a second well of said at least two wells containing antibody or antigen labelled with labelling compound, a cartridge stocker for storing said plurality of reaction cartridges, a reaction line for conveying said plurality of reaction cartridges successively with a predetermined interval and performing a reaction between the sample and a reactive solution and a measurement of the reaction at predetermined positions along said reaction line, a cartridge transportation mechanism for transporting said plurality of reaction cartridges from said cartridge stocker to a starting portion of said reaction line one by one according to an item to be measured, an aspirating/pouring portion disposed in a predetermined position along said reaction line for individually aspirating the plurality of samples stored in said sample stocker portion and the labelled antigen or antibody contained in said second well of each cartridge and pouring them to said first well of each cartridge to obtain a mixture of them, a stirring portion for stirring the mixture contained in said first well of each cartridge, a bind/free separator for separating reacted substance bound with the solid phase material from non-reacted, free substance, a washing portion for removing the non-reacted, free substance, a measuring portion for measuring any information produced from the labelled compound bound with the solid phase material, an output portion for outputting a result of measurements from said measuring portion, a cartridge disposer arranged around an end of said reaction line for disposing of cartridges whose measurements are completed, and a control portion for controlling the operations of all of said reaction line, said cartridge transportation mechanism, said aspirating/pouring portion, said stirring portion, said bind/free separator, said washing portion, said measuring portion, said output portion for outputting a result of measurements from said measuring portion, and said cartridge disposer.

2. The apparatus claimed in claim 1, wherein said solid phase material comprises magnetic particles and wherein said bind/free separator comprises a magnetic separator.

3. The apparatus claimed in claim 1, wherein said labelling compound is an enzyme.

4. The apparatus claimed in claim 1 or 3, wherein each cartridge is formed of optically transparent, non-magnetic material and said measuring portion comprises an optical measuring device.

5. The apparatus claimed in claim 4, wherein said optical measuring device comprises an upright optical cylinder defined in a bock material between an upper opening and a lower opening having a larger diameter than that of said upper opening formed therein, said upright optical cylinder having a tapered reflective wall, said upper opening being adapted to receive a bottom portion of said first well of each cartridge, a filter disposed below said lower opening of said upright optical cylinder and an upright photo multiplier disposed below said filter for detecting luminance of said first well.

6. The apparatus claimed in claim 1, wherein each cartridge is a resin mold including a rectangular plate portion having opposite notched ends and said at least two wells are positioned side by side along a longitude of said rectangular plate portion and extend downwardly therefrom, said first well of each cartridge being deeper than said second well of each cartridge.

7. The apparatus claimed in claim 6, wherein each cartridge includes a third well containing sample or diluent.

8. The apparatus claimed in claim 6 or 7, wherein said solid phase material comprises an inner wall of said first well of each cartridge.

9. The apparatus claimed in claim 6 or 7, wherein said solid phase material comprises beads.

10. The apparatus claimed in claim 6, wherein said labelling compound is an enzyme.

11. An automatic enzyme immunoassay apparatus comprising, in a first level, cartridge transportation means for transporting rectangular cartridges each having at least two successively arranged wells, a first one of said wells containing solid phase material carrying antigen or antibody and a second one of said wells containing enzyme labelled antigen or antibody, to a predetermined position in said first level one by one in sequence, and lift means for lifting up said rectangular cartridges transported thereto by said cartridge transportation means to a second level one by one; and, in said second level, a reaction line movable steppingly with a predetermined interval for receiving said rectangular cartridges lifted up thereto by said lift means at a first position set along said reaction line, successively; pouring means disposed at a second position set along said reaction line for aspirating sample from a sample cassette and pouring it to said first well of said rectangular cartridge moved to said second position; stirring means disposed at a third position along said reaction line for mixing and stirring said sample, said solid phase material carrying antigen or antibody and said enzyme labelled antigen or antibody in said first well of said rectangular cartridge moved to said third position; bind/free separation and washing means disposed in a fourth position along said reaction line for performing bind/free separation in said first well of said rectangular cartridge moved to said fourth position and for removing free components thereof; means disposed at a fifth position along said reaction line for adding substrate to said first well to cause enzyme reaction; optical measuring means for detecting reaction in said first well of said rectangular cartridge after a predetermined time from a start of said enzyme reaction in said first well of said rectangular cartridge, and cartridge disposer means for picking up said rectangular cartridge from said reaction line after said detection completes and disposing it.

12. A method of enzyme immunoassay measurement, comprising the steps of:
actuating a start button of an input portion of an apparatus to start a driving of a reaction line and to transport cartridges in a cartridge stocker one by one to a start position on said reaction line through a cartridge transportation mechanism and a cartridge lift mechanism;
breaking a seal of said cartridges at a first position on said reaction line successively through a seal breaker;
operating a selection button to select one of a plurality of programs stored in a program memory;
actuating an aspirating/pouring portion to pick up a chip, aspirate a sample therein and pour it into a first well of a cartridge at a second position on said reaction line;
after the chip is disposed, actuating said aspirating-/pouring portion again to pick up another chip, aspirate a sample therein and pour it into a second well of said cartridge;
activating a first stirring portion to stir a mixture in said first well of said cartridge at a third position on said reaction line;
performing a B/F separation by a first magnetic B/F separator at a fourth position on said reaction line;
washing out non-reacted free substance by means of a first washing portion at a fifth position on said reaction line;
adding substrate to said first well by a substrate pouring portion and stirring in a second stirring portion at a sixth position on said reaction line; and
measuring a reaction optically by a measuring portion at a seventh position on the reaction line.

13. A method of enzyme immunoassay measurement, comprising the steps of:
actuating a start button of an input portion of an apparatus to start a drive of a reaction line and to transport cartridges in a cartridge stocker one by one to a start position on said reaction line through a cartridge transportation mechanism and a cartridge lift mechanism;
breaking a seal of said cartridges at a first position on said reaction line successively through a seal breaker;
operating a selection button to select one of a plurality of programs stored in a program memory;
actuating an aspirating/pouring portion to pick up a chip, aspirate a sample therein and pour it into a first well of a cartridge at a second position of said reaction line;
after the chip is disposed, actuating said aspirating-/pouring portion again to pick up another chip, aspirate a sample therein and pour it into a second well of said cartridge at a third position on said reaction line;
activating a first stirring portion to stir a mixture in said first well of said cartridge at a fourth position on said reaction line;
pouring said sample into said first well of said cartridge at a fifth position on said reaction line;
performing a B/F separation by a first magnetic B/F separator at a sixth position on said reaction line;
washing out non-reacted free substance by means of a first washing portion at a seventh position on said reaction line;
adding substrate to said first well and stirring it at a seventh position on said reaction line; and
measuring a reaction optically by a measuring portion at a seventh position on the reaction line.

14. A method of enzyme immunoassay measurement, comprising the steps of:
actuating a start button of an input portion of an apparatus to start a drive of a reaction line and to transport cartridges in a cartridge stocker one by one to a start position on said reaction line through a cartridge transportation mechanism and a cartridge lift mechanism;
breaking a seal of said cartridges at a first position on said reaction line successively through a seal breaker;
operating a selection button to select one of a plurality of programs stored in a program memory;
pouring a sample into a first well of a cartridge at a second position on said reaction line;
stirring said first well at a third position on said reaction line;
performing a B/F separation and washing at a third position on said reaction line;
adding an enzyme labelled substance to said first well and stirring it at a fourth position on said reaction line;

performing a B/F separation and washing at a fifth position on said reaction line;

stirring said first well at a sixth position on said reaction line;

performing a B/F separation and washing at a seventh position on said reaction line;

adding a substrate to said first well and stirring it at an eighth position on said reaction line; and measuring a reaction by a measuring portion at a ninth position on said reaction line.

15. A method of enzyme immunoassay measurement, comprising the steps of:

actuating a start button of an input portion of an apparatus to start a drive of a reaction line and to transport cartridges in a cartridge stocker one by one to a start position on said reaction line through a cartridge transportation mechanism and a cartridge lift mechanism;

breaking a seal of said cartridges at a first position on said reaction line successively through a seal breaker;

operating a selection button to select one of a plurality of programs stored in a program memory;

adding diluent to a second well of a cartridge at a second position on said reaction line;

pouring a sample into said second well of said cartridge at a third position on said reaction line;

pouring a portion of a diluted sample in said second well into a first well and stirring it at a fourth position on said reaction line;

performing a B/F separation and washing at a fifth position on said reaction line;

adding an enzyme labelled substance to said first well and stirring it at a sixth position on said reaction line;

performing a B/F separation and washing at a seventh position on said reaction line;

stirring said fist well at an eighth position on said reaction line;

performing a B/F separation and washing at a ninth position on said reaction line;

adding a substrate to said first well and stirring it at a tenth position on said reaction line; and measuring a reaction by a measuring portion at an eleventh position on said reaction line.

* * * * *